(12) United States Patent
Cai et al.

(10) Patent No.: US 7,547,383 B2
(45) Date of Patent: Jun. 16, 2009

(54) BIOSENSOR AND METHOD

(75) Inventors: Xiaohua Cai, Needham, MA (US);
Handani Winarta, Nashua, NH (US);
Chung Chang Young, Weston, MA (US)

(73) Assignee: Nova Biomedical Corporation, Waltham, MA (US)

( * ) Notice: Subject to any disclaimer, the term of this patent is extended or adjusted under 35 U.S.C. 154(b) by 920 days.

(21) Appl. No.: 10/861,670

(22) Filed: Jun. 4, 2004

(65) Prior Publication Data

US 2004/0217019 A1 Nov. 4, 2004

Related U.S. Application Data

(62) Division of application No. 09/919,126, filed on Jul. 31, 2001, now Pat. No. 6,767,441.

(51) Int. Cl.
*G01N 27/327* (2006.01)
(52) U.S. Cl. .............................. 205/777.5; 204/403.03; 204/403.04; 427/125
(58) Field of Classification Search ...............................
204/403.01–403.04, 403.12; 205/777.5, 205/778, 792; 427/125
See application file for complete search history.

(56) References Cited

U.S. PATENT DOCUMENTS

| | | | | |
|---|---|---|---|---|
| 5,120,420 A | * | 6/1992 | Nankai et al. | 204/403.11 |
| 5,582,697 A | * | 12/1996 | Ikeda et al. | 205/777.5 |
| 5,665,222 A | * | 9/1997 | Heller et al. | 205/792 |
| 5,830,341 A | * | 11/1998 | Gilmartin | 205/777.5 |
| 6,103,033 A | * | 8/2000 | Say et al. | 156/73.1 |
| 6,287,451 B1 | * | 9/2001 | Winarta et al. | 205/777.5 |

OTHER PUBLICATIONS

Madaras et al, Analytica Chimica Acta 319, 1996, pp. 335-345.*
Schneider et al, Analytica Chimica Acta 325 (1996), pp. 161-167.*

* cited by examiner

*Primary Examiner*—Kaj K Olsen
(74) *Attorney, Agent, or Firm*—Robert R Deleault, Esq.; Mesmer & Deleault, PLLC

(57) ABSTRACT

An improved biosensor having at least a first working electrode and a first electrode material disposed on the first working electrode. The first electrode material is a mixture made by combining at least one enzyme where the at least one enzyme is a capable of reacting with the analyte to be measured, a redox mediator capable of reacting with a product of an enzymatic reaction or a series of enzymatic reactions involving the at least one enzyme, a peroxidase capable of catalyzing a reaction involving the redox mediator where the redox mediator is oxidized, a binder and a surfactant.

10 Claims, 12 Drawing Sheets

BIOSENSOR AND METHOD

This application is a Divisional application of Ser. No. 09/919,126, filed on Jul. 31, 2001, now U.S. Pat. No. 6,767,441.

BACKGROUND OF THE INVENTION

1. Field of the Invention

The present invention relates generally to a biosensor that can be used for the quantification of a specific component or analyte in a liquid sample. Particularly, this invention relates to a new and improved biosensor and to a new and improved method of fabricating a biosensor for the quantification of a specific component or analyte in a liquid sample such as creatinine, creatine, glucose, cholesterol, urea and the like. More particularly, this invention relates to a disposable biosensor that is inexpensive to manufacture. Even more particularly, this invention relates to a disposable biosensor and method that accurately measures various analytes such as creatinine, creatine, glucose, cholesterol and the like in small volume biological fluid samples. Still even more particularly, this invention relates to a method of measuring the concentration of various analytes in small volume biological fluid samples using a redox mediator and at least an enzyme based on the electrochemical mechanism.

2. Description of the Prior Art

Biosensors have been used in the determination of concentrations of various analytes in fluids for more than three decades. Of particular interest is the measurement of blood glucose, creatinine, creatine, and cholesterol.

It is well known that the concentration of blood glucose is extremely important for maintaining homeostasis. Products that measure fluctuations in a person's blood sugar, or glucose levels, have become everyday necessities for many of the nation's millions of diabetics. Because this disorder can cause dangerous anomalies in blood chemistry and is believed to be a contributor to vision loss and kidney failure, most diabetics need to test themselves periodically and adjust their glucose level accordingly, usually with insulin injections. If the concentration of blood glucose is below the normal range, patients can suffer from unconsciousness and lowered blood pressure that may even result in death. If the blood glucose concentration is higher than the normal range, the excess blood glucose can result in synthesis of fatty acids and cholesterol, and in diabetics, coma. Thus, the measurement of blood glucose levels has become a daily necessity for diabetic individuals who control their level of blood glucose by insulin therapy.

Patients who are insulin dependent are instructed by doctors to check their blood-sugar levels as often as four times a day. To accommodate a normal life style to the need of frequent monitoring of glucose levels, home blood glucose testing was made available with the development of reagent strips for whole blood testing.

One type of blood glucose biosensors is an enzyme electrode combined with a mediator compound that shuttles electrons between the enzyme and the electrode resulting in a measurable current signal when glucose is present. The most commonly used mediators are potassium ferricyanide, ferrocene and its derivatives, as well as other metal-complexes. Many sensors based on this type of electrode have been disclosed. Examples of this type of device are disclosed in the following patents.

U.S. Pat. No. 5,628,890 (1997, Carter et al.) discloses an electrode strip having an electrode support, a reference or counter electrode disposed on the support, a working electrode spaced from the reference or counter electrode on the support, a covering layer defining an enclosed space over the reference and working electrodes and having an aperture for receiving a sample into the enclosed space, and a plurality of mesh layers interposed in the enclosed space between the covering layer and the support. The covering layer has a sample application aperture spaced from the electrodes. The working electrode includes an enzyme capable of catalyzing a reaction involving a substrate for the enzyme and a mediator capable of transferring electrons between the enzyme-catalyzed reaction and the working electrode.

U.S. Pat. No. 5,708,247 (1998, McAleer et al.) discloses a disposable glucose test strip having a substrate, a reference electrode, a working electrode, and a means for making an electrical connection. The working electrode has a conductive base layer and a coating layer disposed over the conductive base layer. The coating layer is a filler having both hydrophobic and hydrophilic surface regions that form a network, an enzyme and a mediator.

U.S. Pat. No. 5,682,884 (1997, Hill et al.) discloses a strip electrode with screen printing. The strip has an elongated support that includes a first and second conductor each extending along the support. An active electrode, positioned to contact the liquid mixture and the first conductor, has a deposit of an enzyme capable of catalyzing a reaction and an electron mediator. A reference electrode is positioned to contact the mixture and the second conductor.

U.S. Pat. No. 5,762,770 (1998, Pritchard et al.) discloses an electrochemical biosensor test strip that has a minimum volume blood sample requirement of about 9 microliters. The test strip has a working and counter electrodes that are substantially the same size and made of the same electrically conducting material placed on a first insulating substrate. Overlaying the electrodes is a second insulating substrate that includes a cutout portion that forms a reagent well. The cutout portion exposes a smaller area of the counter electrode than the working electrode. A reagent for analysis of an analyte substantially covers the exposed areas of the working and counter electrodes in the reagent well. Overlaying the reagent well and affixed to the second insulating substrate is a spreading mesh that is impregnated with a surfactant.

U.S. Pat. No. 5,755,953 (1998, Henning et al.) discloses a reduced-interference biosensor. The device generally comprises an electrode used to electrochemically measure the concentration of an analyte of interest in a solution. The device includes a peroxidase enzyme covalently bound to microparticle carbon and retained in a matrix in intimate contact with the electrode. According to this disclosure, it is the enzyme/microparticle carbon of the device that provides a composition that displays little sensitivity to known interfering substances.

It is well known that creatinine is a waste product derived from creatine and excreted by the kidneys. The analytical determination of creatinine in urine, serum or plasma is a widely used and extremely important test for renal dysfunction. Measurements of creatinine in serum or urine may also be used as indices in the diagnosis and treatment of other disorders such as muscular dystrophy and hypothyroidism. Thus, the creatinine assay has been a widely recognized as having vital medical significance. Further, dietary changes have little if any influence on the creatinine concentration in blood and urine. Although creatinine is primarily a waste product, and as such plays no important role in biochemical functions of the body, its chemical precursor, creatine, has a vital biochemical role. Creatine is a basic building block of creatine phosphate, which is the primary form of energy storage in muscle. As a result, the creatinine level is an important diagnostic index for renal, muscular and thyroid function.

Spectrophotometry has been conventionally employed for measuring creatinine. The presence and concentration of creatinine in the above-mentioned body fluids is most frequently determined by the Jaffe reaction. In this reaction, creatinine reacts with picric acid to produce a red color, a red tautomer of creatinine picrate. This method suffers from serious disadvantages including, but not limited to, the instability of alkaline picrate solutions and the concomitant necessity for preparing solutions as needed, interference from blood metabolites, the analytical time required to perform the method, and the lack of specificity.

Sensors have been developed for the detection of creatinine based on enzymatic cleavage of creatinine. Among them, electrochemical methods received particular attention. Rechnitz et. al. (T. Huvin and G. A. Rechnitz, Anal. Chem., 46 (1974) 246) used creatinine deiminase coupled with an ammonia electrode to measure ammonia produced by an enzymatic reaction. However, this potentiometric method seems of little usefulness due to serious interference problems and the sensitivity limitation of the gas-sensing electrode.

U.S. Pat. No. 5,958,786 (1999, C. Munkholm) provides for the coupling of the enzymatic cleavage of creatinine to detection by a fluorescent polymer coating. The polymer coating has a first layer of protonated pH sensitive fluorophore immobilized in a hydrophobic polymer. The fluorophore reacts quantitatively with ammonia. The transducing moiety of the fluorophore is neutrally charged when deprotonated. The polymer coating has a second layer of creatinine deiminase and a polymer, and a third layer of a polymer. A disadvantage of this device is that two consecutive readings must be made. First, a fluorescence measurement must be made of the creatinine sensor. Second, the sensor material of the creatinine sensor is then exposed to a solution containing creatinine followed by measuring the fluorescence change and determining the concentration of creatinine.

A more practical strategy was reported by Tsuchida and Yoda in 1983 (T. Tsuchida and K. Yoda, Clin. Chem., 29/1 (1983) 51). The proposed system consisted of three enzymes, creatinine amidohydrolase (C1), creatine amidinohydrolase (C2) and sarcosine oxidase (SO). These enzymes were co-immobilized onto the porous side of a cellulose membrane. The membrane was combined with a polarographic electrode for sensing hydrogen peroxide, a product resulting from the enzymatic reaction. Several research groups attempted to improve electrode performance through better enzyme immobilization techniques. (H. Yamato, M. Ohwa and W. Wernet, Anal. Chem., 67 (1995) 2776; M. B. Madaras, I. C. Popescu, S. Ufer and R. P. Buck, Anal. Chim. Acta, 319 (1996) 335; J. Schneider, B. Grundig, R. Renneberg, K. Camman, M. B. Madaras, R. P. Buck and K.D. Vorlop, Anal. Chim. Acta, 325 (1996) 161). Despite the improvements in enzyme immobilization, the methods suffer from various shortcomings including long-term stability, appropriate dynamic measurement range and serious interference from other oxidizable substances in the sample fluid such as ascorbic acid and acetaminophen as well as creatine.

Currently, two commercial products for measuring blood creatinine are available. One is from Nova Biomedical Corporation. It is a critical care analyzer that provides a complete 14-test profile from as little as 105 microliters of whole blood where one of the tests is for creatinine. The creatinine sensor is a multiple-use, membrane-based sensor arranged in a fluid channel along with other biosensors (Nova Stat Profile® M, Nova Biomedical Corporation, Waltham, Mass.). The enzymes are immobilized onto the membrane and the membrane is attached to the working electrode (platinum) and the reference electrode (Ag—AgCl).

The second commercial product is from i-Stat Corporation (Kanata, Ontario, Canada). A US patent covers this product. U.S. Pat. No. 5,554,339 (1996, Cozzette et al.) discloses an amperometric base sensor fabricated on a planar silicon substrate by means of photolithography in combination with the plasma deposition of metallic substances. The metallic substances include iridium metal (used as working electrode) and silver metal (served as reference electrode along with resulting chloridized silver). Three enzymes (C1, C2 and SO) are immobilized onto the electrodes as an overlaid structure. The above two products require calibration before measurement and a relatively large amount of sample volume. They also require a relatively longer waiting time for test results.

Because of the significance of obtaining accurate analyte concentration measurements, it is highly desirable to develop a reliable, user-friendly and disposable sensor, which does not have all of the drawbacks previously mentioned. Therefore, what is needed is an electrochemical sensor that does not require routine maintenance. What is further needed is an improved electrochemical sensor that combines peroxidase with a mediator. What is still further needed is an improved electrochemical sensor that combines peroxidase with a mediator and that operates at a reductive potential where interferents are not oxidized. What is yet further needed is an improved creatinine electrochemical sensor that includes an interference-correcting electrode to minimize the interference effects caused by the presence of creatine in a sample fluid. What is yet further needed are improved electrochemical sensors for cholesterol, glucose and other biologically important metabolites. Yet, what is still further needed is an electrochemical sensor that requires less sample volume for measuring an analyte than previously required by the prior art. What is still further needed is an improved disposable sensor for self-testing.

SUMMARY OF THE INVENTION

It is an object of the present invention to provide an electrochemical sensor that does not require routine maintenance. It is a further object of the present invention to provide an electrochemical sensor that combines at least one enzyme with a peroxidase and a mediator. It is still a further object of the present invention to provide an electrochemical sensor that combines at least one enzyme with a peroxidase and a mediator and that operates at a lower potential where interferents are not oxidized. It is yet a further object of the present invention to provide a creatinine electrochemical sensor that includes an interference-correcting electrode to minimize the interference effects caused by the presence of creatine in a sample fluid. It is yet further object of the present invention to provide improved electrochemical sensors for cholesterol, glucose and other biologically important metabolites. It is yet another object of the present invention to provide an electrochemical sensor with high sensitivity to the analytes to be measured. It is yet still a further object of the present invention to provide an electrochemical sensor that requires less sample volume for measuring analytes than previously required by the prior art. It is still a further object of the present invention to provide an improved disposable sensor for self-testing.

The present invention achieves these and other objectives by providing a simple and convenient method of measuring various analytes in biological fluids. Although the following describes a preferred design of the present invention, a sensor of the present invention may have different physical shapes without detracting from the unique characteristics of the present invention. The present invention has a laminated, elongated body having a sample fluid channel connected between an opening on one end of the laminated body and a vent hole spaced from the opening. Within the fluid channel lie one or more working electrodes and a reference electrode, depending on the analyte to be measured. The arrangement of the one or more working electrodes and the reference electrode is not important for purposes of the results obtained from the sensor. The working electrodes and the reference electrode are each in electrical contact with separate conductive conduits, respectively. The separate conductive conduits terminate and are exposed for making an electrical connection to a reading device on the end opposite the open channel end of the laminated body.

The laminated body has a base insulating layer made from a plastic material. Several conductive conduits are delineated on the base insulating layer. The conductive conduits may be deposited on the insulating layer by screen printing, by vapor deposition, or by any method that provides for a conductive layer that adheres to the base insulating layer. The conductive conduits may be individually disposed on the insulating layer, or a conductive layer may be disposed on the insulating layer followed by etching/scribing the required number of conductive conduits. The etching process may be accomplished chemically, by mechanically scribing lines in the conductive layer, by using a laser to scribe the conductive layer into separate conductive conduits, or by any means that will cause a break between and among the separate conductive conduits required by the present invention. Conductive coatings or layers that may be used are coatings of copper, gold, tin oxide/gold, palladium, other noble metals or their oxides, or carbon film compositions. The preferred conductive coatings are gold film or a tin oxide/gold film composition.

It should be pointed out that although the same electrically conducting substance (gold film or tin oxide/gold film) after scoring is used as conducting material for both the one or more working electrodes and the reference electrode, this material itself cannot function as a reference electrode. To make the reference electrode work, there must be a redox reaction (e.g., $Fe(CN)_6^{3-} + e^- \leftrightarrow Fe(CN)_6^{4-}$ or $AgCl + e^- \leftrightarrow Ag + Cl^-$) at the electrically conducting material when a potential is applied. Therefore, a redox reaction must be present at the conducting material used for the reference electrode.

In one embodiment of the present invention, the laminated body has a first middle insulating layer, also called a reagent holding layer, on top of the base insulating layer and the conductive conduits. The first middle layer, or reagent holding layer, contains cutouts for one or more working electrodes and a reference electrode. Each cutout corresponds to and exposes a small portion of a single conductive conduit. The cutouts for the working electrodes are substantially the same size. The cutout for the reference electrode may be the same or different size as the cutouts for the working electrodes. The placement of all of the cutouts is such that they will all co-exist within the sample fluid channel described above. This first middle insulating layer is also made of an insulating dielectric material, preferably plastic, and may be made by die cutting the material mechanically or with a laser and then fastening the material to the base layer. An adhesive, such as a pressure-sensitive adhesive, may be used to secure the first middle insulating layer to the base layer. Adhesion may also be accomplished by ultrasonically bonding the first middle layer to the base layer. The first middle insulating layer may also be made by screen printing the first middle insulating layer over the base layer.

Each cutout contains electrode material. The electrode material has a redox mediator and a peroxidase. The peroxidase may be from any source such as soybean (soybean peroxidase (SBP)) or horseradish root (horseradish root peroxidase (HRP)). For most analytes such as glucose and cholesterol, at least one of the cutouts contains the electrode material and an analyte-related enzyme forming an enzyme mix capable of catalyzing a reaction involving a substrate for the enzyme, e.g. glucose oxidase (GOD) for glucose. The redox mediator is capable of transferring electrons between the enzyme-catalyzed reactions and the working electrode.

For analytes having a substrate capable of undergoing similar reactions and causing an interference effect, a multiple enzyme mix may be required. Creatinine is one such analyte. Both creatinine and creatine exist in the blood. To measure the enzyme creatinine using the present invention, at least one "working electrode" cutout contains the electrode material and two enzymes, e.g. creatine amidinohydrolase (C2) and sarcosine oxidase (SO), capable of catalyzing a reaction involving a substrate for the enzyme creatine. This measures the creatine level. A second cutout contains the electrode material and three enzymes, e.g. creatinine amidohydrolase (C1), creatine amidinohydrolase and sarcosine oxidase, capable of catalyzing a reaction involving a substrate for the enzyme creatinine. The difference in output of the two working electrodes represents the concentration of creatinine in the samples.

The enzymatic-reaction sequence for a creatinine sensor is:

$$\text{Creatinine} + H_2O \xrightarrow{C1} \text{Creatine} \quad \text{Eq. (1)}$$

$$\text{Creatine} + H_2O \xrightarrow{C2} \text{Sarcosine} + \text{Urea} \quad \text{Eq. (2)}$$

$$\text{Sarcosine} + H_2O + O_2 \xrightarrow{SO} \text{Glycine} + HCHO + H_2O_2 \quad \text{Eq. (3)}$$

Creatinine measurements in the prior art are based on the amperometric detection of $H_2O_2$ resulting from the above enzymatic reaction. The enzymatic-reaction sequence for a glucose sensor is:

$$\text{Glucose} + H_2O + O_2 \xrightarrow{GOD} \text{Gluconic acid} + H_2O_2 \quad \text{Eq. (4)}$$

The present invention increases the sensitivity of the analyte measurement by incorporating a mediator and a peroxidase enzyme in the electrode material. The preferable mediators are redox chemicals either in oxidized or reduced form. The mediator used in the present invention may be at least one of a variety of chemicals in their reduced form, or virtually any oxidizable species or electron donors. Examples of useable compounds are $Fe(CN)_6^{3-}$, $Fe(CN)_6^{4-}$, $Fe(phen)_3^{2+}$ (phen=1,10-phenanthroline), $Fe(bpy)_3^{2+}$ (bpy=2,2'-bipyridine), $Co(NH_3)_6^+$, $Co(phen)_3^{2+}$, $Co(bpy)_3^{2+}$, $Os(bpy)_2Cl^+$, $Os(phen)_2Cl^+$ $Ru(bpy)_2^{2+}$, $Rh(bpy)_2^{2+}$, cobalt phthalocyanine, various ferrocenes, methylene blue, methylene green, 7,7,8,8-tetracyanoquinodimethane (TCNQ), tetrathiafulvalene (TTF), toluidine blue, meldola blue, N-methylphenazine methosulfate, phenyldiamines, 3,3',5,5'-tetramethylbenzidine (TMB), pyrogallol, and benzoquinone (BQ). It is desirable that the mediator is capable of being oxidized chemically by hydrogen peroxide resulting from the enzymatic reactions such as those illustrated in Eqs. (1) to (3) and Eq. (4) above. It is further desirable that the oxidation form of the mediator is capable of being reduced electrochemically at the working electrodes at the applied potential. It is still further desirable that the mediator is stable in the matrix. The preferred mediator in the present invention is potassium ferrocyanide ($K_4Fe(CN)_6$).

The reduced form of the ferrocyanide mediator ($Fe(CN)_6^{4-}$) is capable of being oxidized by the hydrogen peroxide resulting from the above enzymatic reaction to $Fe(CN)_6^{3-}$ in the presence of a peroxidase. When using ferrocyanide as the mediator, the oxidation reaction is as shown below:

$$Fe(CN)_6^{4-} + H_2O_2 \xrightarrow{SBP} Fe(CN)_6^{3-} + H_2O \quad \text{Eq. (5)}$$

The oxidized form of the ferrocyanide radical ($Fe(CN)_6^{3-}$) is capable of being reduced electrochemically when a low potential is applied to the working electrodes. The resulting current signal is related to the analyte concentration.

It is well known that dissolved oxygen could be reduced at the electrode when a low potential is applied. Thus, it is desirable to apply a potential between the working electrodes and the reference electrode such that $Fe(CN)_6^{3-}$ is electro-reduced but dissolved oxygen is not or minimized. Furthermore, it is also desirable to use a potential where the electro-oxidation of other oxidizable interferents like ascorbic acid and acetaminophen either does not occur or is minimal. An example of such an applied potential is between about 0.0 V and about −0.6 V as measured against the reference electrode of the present invention. The preferred potential is about −0.15 V. This potential is preferred for providing a good ratio of signal vs. background noise/interference.

It is also desirable to minimize the interference from hematocrit (volume fraction of erythrocytes) on the results. Because the conductivity (or impedance) of whole blood is dependent on hematocrit, it can then be used to correct the effect of hematocrit on the reported concentration.

The resistance (r-value) between W (working electrode) and R (reference electrode) is related to the hematocrit as represented by the following equation:

$$r = k_1/(1-H) \quad \text{Eq.(6)}$$

where
 r is resistance value measured in Ohms or Kilo-Ohms
 H is hematocrit level
 $k_1$ is a constant (r measured in Kilo-Ohms)

The measured "r" can then be used to correct the analyte concentration. The relationship is represented by the Equation (7).:

$$C_{corr} = k_2 \times C_{mea} \times r/r_o \quad \text{Eq.(7)}$$

where
 $C_{corr}$ is the corrected analyte concentration
 $C_{mea}$ is the measured analyte concentration
 $r_o$ is the resistance value in Ohms or Kilo-Ohms measured at a preselected normal hematocrit
 $k_2$ is a constant The laminated body also has a second middle insulating layer, also called a channel-forming layer, on top of the first middle layer. The second middle layer, or channel-forming layer is also made of a plastic insulating material and creates the sample fluid channel of the laminated body. It contains a U-shaped cutout on one end which overlays the cutouts on the first middle layer with the open end corresponding to the open end of the laminated body described earlier.

The laminated body of the present invention has a top layer with a vent opening. The vent opening is located such that at least a portion of the vent opening overlays the bottom of the U-shaped cutout of the second middle insulating layer. The vent allows air within the sample fluid channel to escape as the sample fluid enters the open end of the laminated body. The sample fluid generally fills the sample fluid channel by capillary action. In small volume situations, the extent of capillary action is dependent on the hydrophobic/hydrophilic nature of the surfaces in contact with the fluid undergoing capillary action. This is also known as the wetability of the material. Capillary forces are enhanced by either using a hydrophilic insulating material to form the top layer, or by coating at least a portion of one side of a hydrophobic insulating material with a hydrophilic substance in the area of the top layer that faces the sample fluid channel between the open end of the laminated body and the vent opening of the top layer. It should be understood that an entire side of the top layer may be coated with the hydrophilic substance and then bonded to the second middle layer.

The insulating layers of the laminated body may be made from any dielectric material. The preferred material is a plastic material. Examples of acceptable compositions for use as the dielectric material are polyvinyl chloride, polycarbonate, polysulfone, nylon, polyurethane, cellulose nitrate, cellulose propionate, cellulose acetate, cellulose acetate butyrate, polyester, acrylic, and polystyrene.

In a second embodiment of the present invention, a first middle layer is not required for those analyte-measuring electrode systems where there are no competing substrate reactions for the enzyme. In other words, where there is no need for a second working electrode such as in the creatinine measuring system of the present invention.

In the embodiments using a first insulating layer, two cutouts contain material for the working electrodes (W1 and W2) and one for the reference electrode (R). The positional arrangement of the two working electrodes and the reference electrode in the channel are not critical for obtaining useable results from the electrochemical sensor. The possible electrode arrangements within the sample fluid channel may be W1-W2-R, W1-R-W2, R-W1-W2, W2-W1-R, W2-R-W1, or R-W2-W1 with the arrangement listed as the arrangement of electrodes would appear from the open end of the laminated body to the vent opening. The preferred position was found to be W1-R-W2; that is, as the sample fluid entered the open end of the laminated body, the fluid would cover W1 first, then R, then W2. The working electrodes and the reference electrode are each in electric contact with separate conductive conduits, respectively. The separate conductive conduits terminate and are exposed for making an electric connection to a reading device on the end opposite the open channel end of the laminated body.

In the creatinine sensor, the first working electrode (W1) is loaded with a mixture of C2, SO, a peroxidase, potassium ferrocyanide, at least one binder, and a surfactant. The second working electrode (W2) is loaded with the same chemical reagent as W1 but with the addition of C1. The reference electrode (R) cutout is loaded with a mixture containing at least one of the redox mediators mentioned above, at least one binder, and a surfactant. It should be noted that W1 is substantially a creatine sensor, while W2 is substantially a sensor responding to creatinine and to creatine. The difference between the electrode responses at W2 and W1 corresponds to the creatinine concentration.

In a glucose sensor, the first working electrode is loaded with a mixture of glucose oxidase, a peroxidase, potassium ferrocyanide, at least one binder, and a surfactant. In a cholesterol sensor, the first working electrode is loaded with a mixture of cholesterol esterase, cholesterol oxidase, a peroxidase, potassium ferrocyanide, at least one binder, and a surfactant. The reference electrode may be loaded with the same mixture as the working electrode. It should be pointed out that the reference electrode cutout could be loaded with a Ag/AgCl layer (e.g. by applying Ag/AgCl ink or by sputter-coating a Ag or Ag/AgCl layer) or other reference electrode materials instead of a redox mediator.

As mentioned earlier, oxidizable interferents such as ascorbic acid, uric acid and acetaminophen, to name a few, cause inaccurate readings in the output of an electrochemical biosensor. The present invention reduces this effect considerably by using an applied potential that minimizes oxidation of these interferents. Also important is the composition of the reagents disposed on W1 and W2. The reagents are designed to have a minimal effect on the response of the interferences which also contributes to the accuracy of the analyte measurement.

All of the advantages of the present invention will be made clearer upon review of the detailed description, drawings and appended claims.

DETAILED DESCRIPTION OF THE PREFERRED EMBODIMENT

Figure 1:
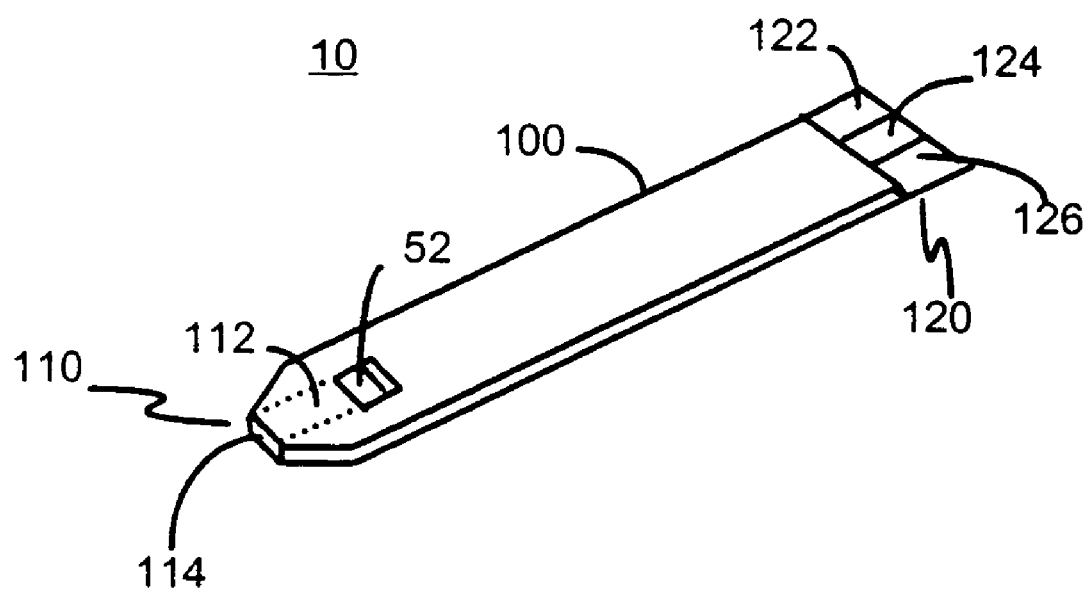
FIG. 1 is a perspective view of the four-layer embodiment of the present invention showing the open end, the vent and the electrical contact points of the laminated body.

The preferred embodiment of the present invention is illustrated in FIGS. 1-13. FIG. 1 shows a sensor 10 of the present invention using the 4-layer construction. Sensor 10 has a laminated body 100, a fluid sampling end 110, an electrical contact end 120, and a vent opening 52. Fluid sampling end 110 includes a sample fluid channel 112 between a sampling end aperture 114 and vent opening 52. Electrical contact end 120 has at least three discreet conductive contacts 122, 124 and 126.

Figure 2:
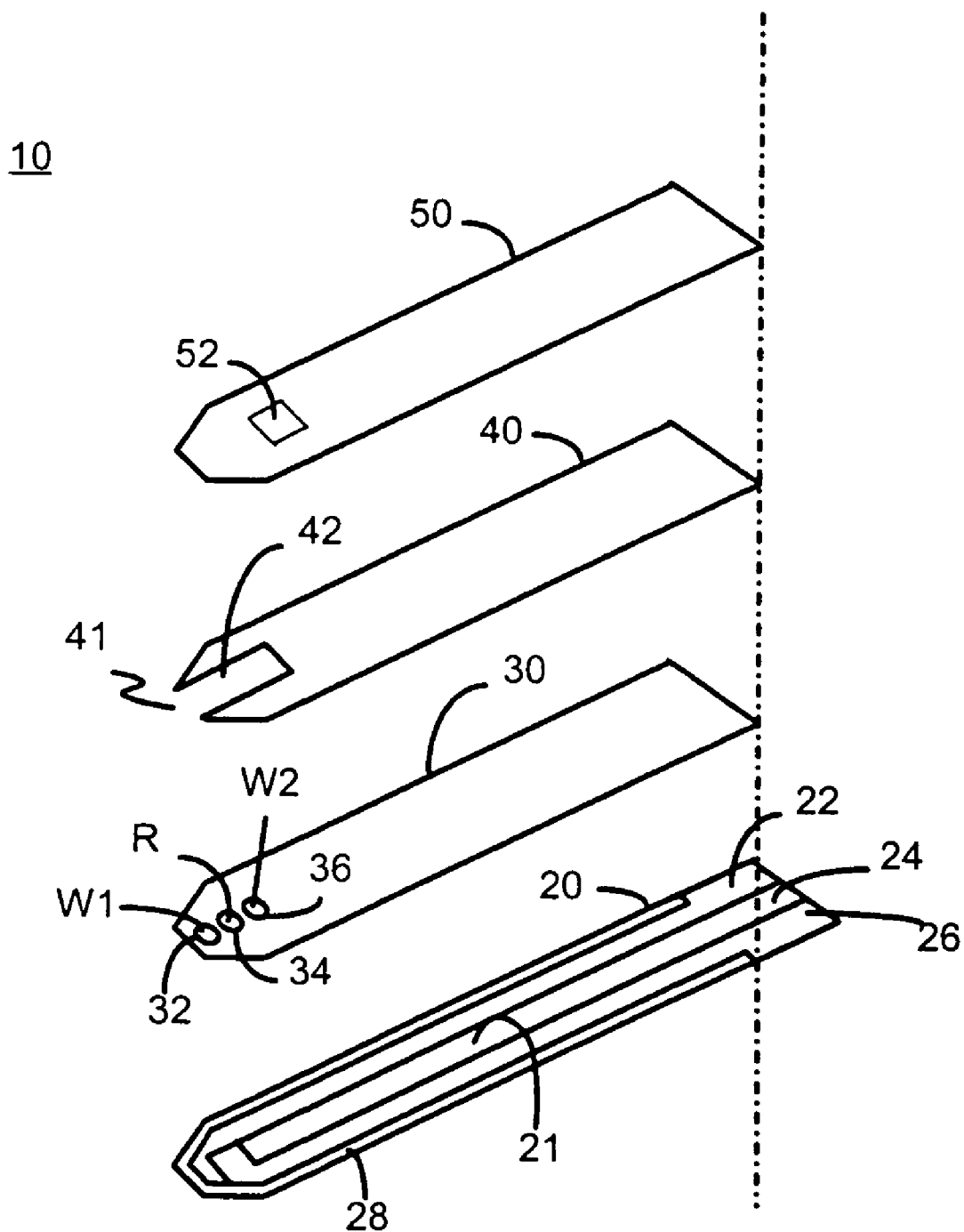
FIG. 2 is an exploded, perspective view of the four-layer embodiment showing the various layers of the laminated body.

Referring now to FIG. 2, laminated body 100 is composed of a base insulating layer 20, a first middle layer 30, a second middle layer 40, and a top layer 50. All layers are made of a dielectric material, preferably plastic. Examples of a preferred dielectric material are polyvinyl chloride, polycarbonate, polysulfone, nylon, polyurethane, cellulose nitrate, cellulose propionate, cellulose acetate, cellulose acetate butyrate, polyester, acrylic and polystyrene. Base insulating layer 20 has a conductive layer 21 on which is delineated a first conductive conduit 22, a second conductive conduit 24 and a third conductive conduit 26. Conductive conduits 22, 24 and 26 may be formed by scribing or scoring the conductive layer 21, as illustrated in FIG. 2, or by silk-screening the conductive conduits 22, 24 and 26 onto base layer 20. Scribing or scoring of conductive layer 21 may be done by mechanically scribing the conductive layer 21 sufficiently to create the three independent conductive conduits 22, 24 and 26. The preferred scribing or scoring method of the present invention is done by using a carbon dioxide ($CO_2$) laser, a YAG laser or an eximer laser. An additional scoring line 28 (enlarged and not to scale; for illustrative purposes only) may be made, but is not necessary to the functionality of sensor 10, along the outer edge of base layer 20 in order to avoid potential static problems which could give rise to a noisy signal. Conductive layer 21 may be made of any electrically conductive material like copper, gold, tin oxide/gold, palladium, other noble metals or their oxides, or carbon film compositions, preferably gold or tin oxide/gold. A useable material for base layer 20 is a tin oxide/gold polyester film (Cat. No. FM-1) or a gold polyester film (Cat. No. FM-2) sold by Courtaulds Performance Films, Canoga Park, Calif.

First middle layer 30 has a first electrode cutout 32 which exposes a portion of first conductive conduit 22, a second electrode cutout 34 which exposes a portion of second conductive conduit 24 and a third electrode cutout 36 which exposes a portion of third conductive conduit 26. First middle layer 30 is made of a plastic material, preferably a medical grade one-sided tape available from Adhesive Research, Inc., of Glen Rock, Pa. Acceptable thicknesses of the tape for use in the present invention are in the range of about 0.001 in. (0.025 mm) to about 0.005 in. (0.13 mm). One such tape, Arcare® 8666 (about 0.003 in. (0.075 mm)), was preferred because of its ease of handling and it showed good performance in terms of its ability to hold a sufficient quantity of chemical reagents and to promote capillary action through sample fluid channel 112 of sensor 10. It should be understood that the use of a tape is not required. A plastic insulating layer may be coated with a pressure sensitive adhesive, or may be ultrasonically-bonded to base layer 20, or may be silk-screened onto base layer 20 to achieve the same results as using the polyester tape mentioned.

The three cutouts 32, 34 and 36 define electrode areas W1, R and W2, respectively, and hold chemical reagents forming two working electrodes and one reference electrode. For biosensors measuring analytes such as glucose and cholesterol, only two cutouts are required that hold chemical reagents for a working electrode and a reference electrode. Typically, electrode area R must be loaded with a redox reagent or mediator to make the reference electrode function. If R is not loaded with a redox reagent or mediator, working electrodes W1 and W2 will not work properly. The redox reagent preferably contains an oxidized form of a redox mediator, at least one binder, and a surfactant. R could also be loaded or coated with silver/silver chloride or other reference electrode materials.

Examples of useable redox mediators are $Fe(CN)_6^{3-}$, $Fe(CN)_6^{4-}$, $Fe(phen)_3^{2+}$ (phen=1,10-phenanthroline), $Fe(bpy)_3^{2+}$ (bpy=2,2'-bipyridine), $Co(NH_3)_6^{2+}$, $Co(phen)_3^{2+}$, $Co(bpy)_3^{2+}$, $Os(bpy)_2Cl^+$, $Os(phen)_2Cl^+Ru(bpy)_2^{2+}$, $Rh(bpy)_2^{2+}$, cobalt phthalocyanine, various ferrocenes, methylene blue, methylene green, 7,7,8,8-tetracyanoquinodimethane (TCNQ), tetrathiafulvalene (TTF), toluidine blue, meldola blue, N-methylphenazine methosulfate, phenyldiamines, 3,3',5,5'-tetramethylbenzidine (TMB), pyrogallol, and benzoquinone (BQ). Silver/silver chloride or other reference electrode materials could also be used.

The redox mediator may be any inorganic or organic redox species. The mediator may also be in either the reduced or oxidized form. Because a low applied potential (−0.15 V) is used in the present invention for detecting the reduction current signal of the product of the enzymatic reaction, if a mediator is used for the reference electrode instead of Ag/AgCl, a reduced form of the redox mediator is preferred for the reference electrode. Use of the reduced form of the redox mediator will minimize carry-over from the reference electrode R to the working electrodes, W1 and W2, which is more likely to occur if an oxidized form of the redox mediator is used at the reference electrode R.

It is preferable that the mediator is capable of being oxidized chemically by hydrogen peroxide resulting from enzymatic reactions such as those illustrated in Eqs. (1) to (3) or Eq. (4) above. It is further desirable that the oxidized form of the mediator is capable of being reduced electrochemically at the working electrodes at the applied potential. It is still further desirable that the mediator is stable in the matrix. The preferred mediator in the present invention is potassium ferrocyanide ($K_4Fe(CN)_6$). The preferred binders are polyethylene oxide and various water soluble cellulose materials like methyl cellulose and the preferred surfactant is t-octylphenoxypolyethoxyethanol.

Generally, electrode area W1 is loaded with a reagent containing chemical components similar to that loaded in electrode area R. These similarities will become clearer to those skilled in the art when the reagent mixes are later described in more detail. The difference between the reagents loaded in W1 and R is that the reagent loaded in electrode area W1 also contains a peroxidase capable of being catalytically reactive with the mediator and at least one enzyme capable of catalyzing a reaction involving the analyte to be measured.

For a creatine sensor, the reagent preferably contains three enzymes, a reduced form of a redox mediator, at least one binder, and a surfactant. The enzymes are preferably creatine amidinohydrolase (C2) sarcosine oxidase (SO) and the peroxidase. The peroxidase may be from any source such as soybean (soybean peroxidase (SBP)) or horseradish root (horseradish root peroxidase (HRP)).

For a glucose sensor, the reagent preferably contains two enzymes, a reduced form of a redox mediator, at least one binder, and a surfactant. The enzymes are preferably glucose oxidase (GOD) and the peroxidase mentioned above.

For a cholesterol sensor, the reagent preferably contains three enzymes, a reduced form of a redox mediator, at least one binder, and a surfactant. The enzymes are preferably cholesterol esterase, cholesterol oxidase and the peroxidase mentioned above.

For the creatinine sensor, electrode area W2 is preferably loaded with the same chemical reagents loaded into electrode area W1 but with the addition of another enzyme (fourth enzyme). This other enzyme is also capable of catalyzing a reaction involving a substrate for the enzyme. The mediator must be capable of transferring electrons transferred between the enzyme-catalyzed reaction and the working electrode to create a current representative of the concentration of the substrate and, more specifically, representative of the concentration of creatinine. The fourth enzyme is preferably creatinine amidohydrolase (C1).

The cutouts and electrode areas of first middle layer 30 are positioned relative to each other and to the flow of the sample fluid in sample fluid channel 112 such that the possible carryover from one electrode area to another electrode area could be minimized. Using fluid sample end 110 of sensor 10 as a reference point, the arrangements of the electrode areas could be W1-W2-R, W1-R-W2, R-W1-W2, W2-W1-R, W2-R-W1, or R-W2-W1. The preferred position for analytes having more than one competing substrate reaction such as the creatinine sensor was found to be W1-R-W2. The preferred position for analytes having only one substrate reaction such as glucose and cholesterol was found to be R-W1-W2.

Second middle layer 40 has a U-shaped channel cutout 42 located at second layer sensor end 41. The length of channel cutout 42 is such that when second middle layer 40 is layered on top of first middle layer 30, electrode areas W1, W2 and R are within the space defined by channel cutout 42. The thickness of second middle layer 40 was found to be important for the speed of the sample fluid flow into sample fluid channel 112, which is filled by capillary action of the sample fluid.

Top layer 50, which is placed over second middle layer 40, has a vent opening 52 spaced from fluid sample end 110 of sensor 10 to insure that sample fluid in fluid channel 112 will completely cover electrode areas W1, W2 and R. Vent opening 52 is placed in top layer 50 so that it will align somewhat with the bottom of channel cutout 42 of second middle layer 40. Preferably, vent opening 52 will expose a portion of and partially overlay the bottom of the U-shaped cutout 42 of second middle layer 40.

Figure 3:
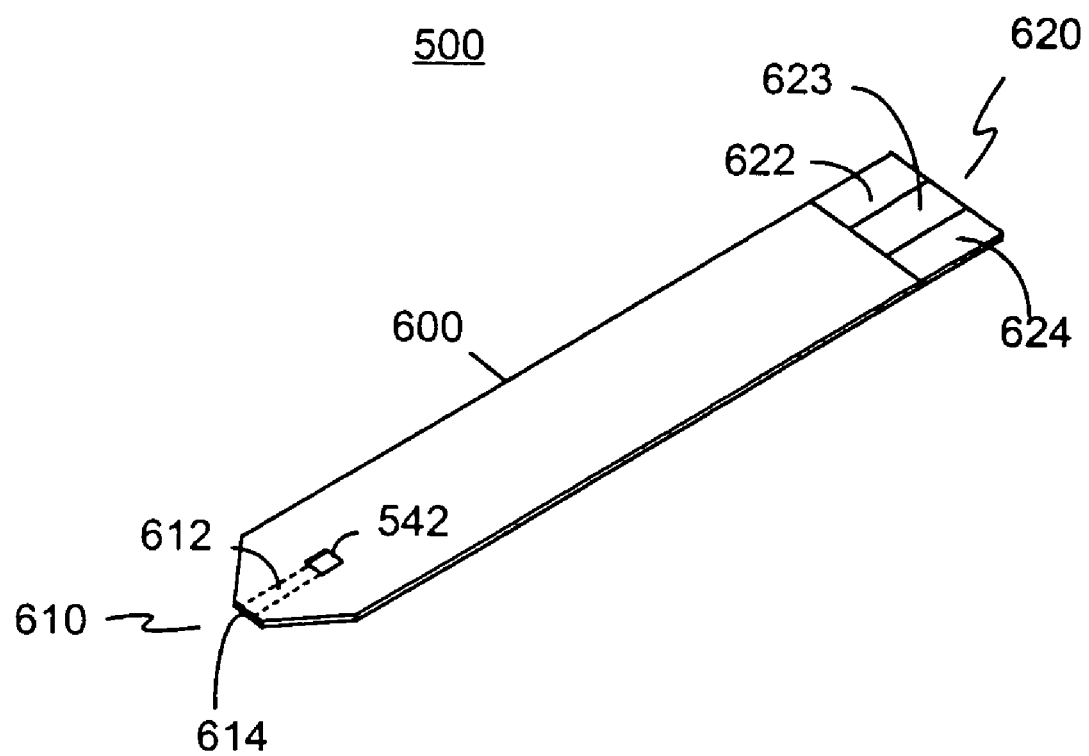
FIG. 3 is a perspective view of the three-layer embodiment of the present invention showing the open end, the vent and the electrical contact points of the laminated body.

FIG. 3 shows another embodiment of the present invention showing a sensor 500 of the present invention using 3-layer construction. Sensor 500 has a laminated body 600, a fluid sampling end 610, an electrical contact end 620, and a vent opening 542. Fluid sampling end 610 includes a sample fluid channel 612 between a sampling end aperture 614 and vent opening 542. Electrical contact end 620 has three discreet conductive contacts 622, 623 and 624.

Figure 4:
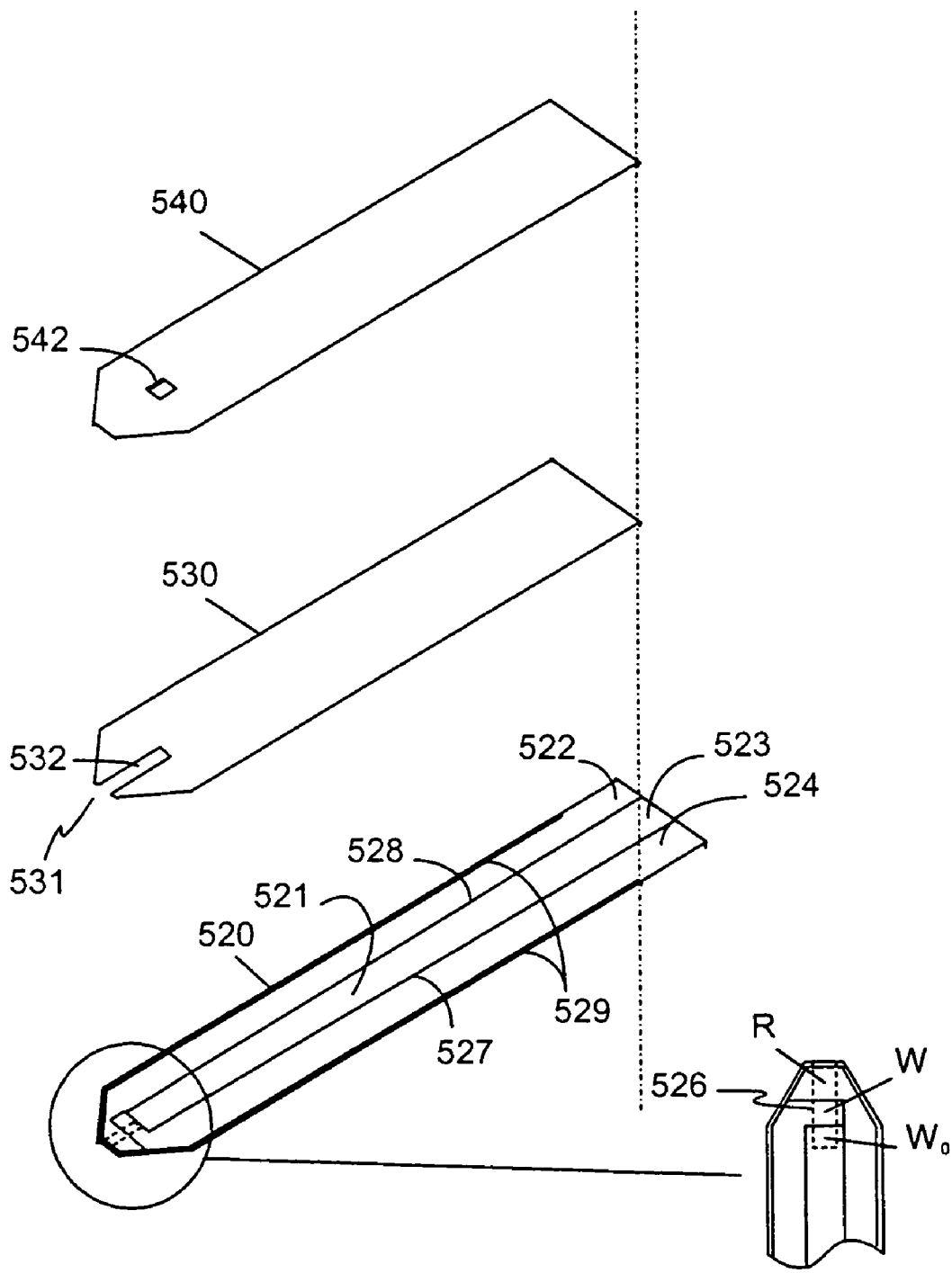
FIG. 4 an exploded, perspective view of the three-layer embodiment showing the various layers of the laminated body.

Referring now to FIG. 4, laminated body 600 is composed of a base insulating layer 520, a middle layer 530, and a top layer 540. All layers are made of a dielectric material, preferably plastic. Base insulating layer 520 has a conductive layer 521 on which is delineated a first conductive conduit 522, a second conductive conduit 523 and a third conductive conduit 524. Conductive conduits 522, 523 and 524 may be formed by scribing or scoring the conductive layer 521 as illustrated in FIG. 4 and shown as scribe line 527 and 528 or by silk-screening the conductive conduits 522, 523 and 524 onto base layer 520. Scribing or scoring of conductive layer 521 may be done by mechanically scribing the conductive layer 521 sufficiently to create the three independent conductive conduits 522, 523 and 524. The preferred scribing or scoring method of the present invention has been previously disclosed. An additional scoring line 529 (enlarged and not to scale; for illustrative purposes only) may be made, but is not necessary to the functionality of sensor 500, along the outer edge of base layer 520 in order to avoid potential static problems which could give rise to a noisy signal.

Figure 5:
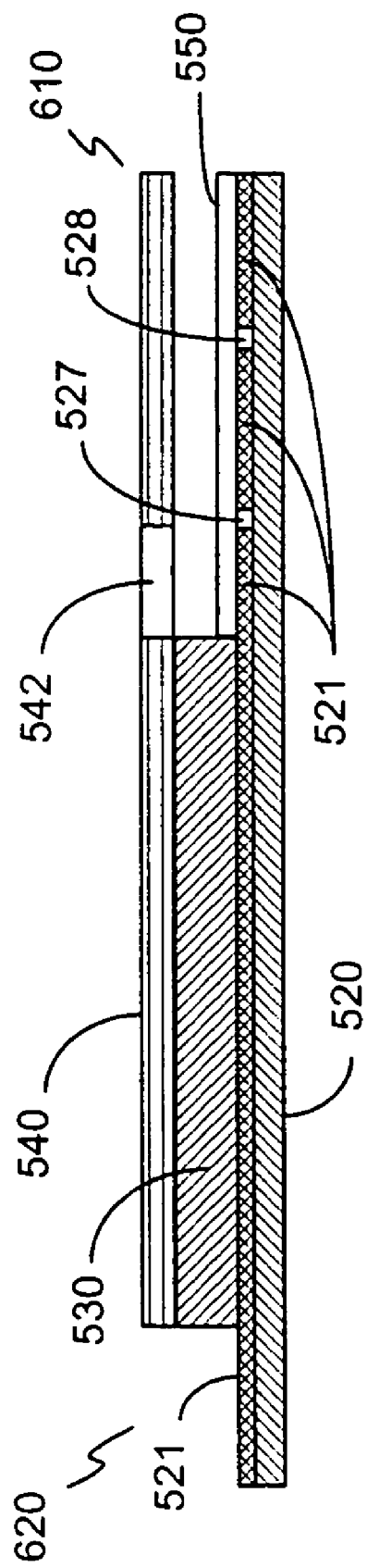
FIG. 5 is a cross-sectional view of the present invention of FIG. 3.

Middle layer 530 has a U-shaped channel cutout 532 located at middle layer sensor end 531. The length of channel cutout 532 is such that when middle layer 530 is layered on top of base layer 520, electrode areas W, R and $W_0$ are within the space defined by channel cutout 532. The thickness of middle layer 530 was found to be important for the speed of the sample fluid flow into sample fluid channel 612, which is filled by capillary action of the sample fluid. Channel cutout 532 along with the base layer 520 holds the reagent matrix 550, more clearly shown in FIGS. 3-5. Channel cutout 532 also defines the area of the working electrode, the reference electrode and the second electrode. Electrode areas W, $W_0$ and R are loaded preferably with the same chemical reagent. The reagents preferably contain a reduced form of a redox mediator, at least one binder, a surfactant, and at least one enzyme. Top layer 540, which is placed over and coextensive with middle layer 530, has a vent opening 542 spaced from fluid sample end 610 of sensor 500 to insure that sample fluid in fluid channel 612 will completely cover electrode areas W, R and $W_0$. Vent opening 542 is placed in top layer 540 so that it will align somewhat with the bottom of channel cutout 532 of middle layer 530, the bottom meaning the channel cutout 532 located furthest from sensor end 531. Preferably, vent opening 542 will expose a portion of and partially overlay the bottom of the U-shaped cutout 532 of middle layer 530. FIG. 5 shows an enlarged cross-sectional view of the various layers of the present invention. The layers are not to scale in order that the relationship of each component of the present invention may be better understood by those skilled in the art, especially scribe lines 27 and 28.

The possible electrode arrangements within the sample fluid channel may be W-R-$W_0$, W-$W_0$-R, R-W-$W_0$, R-$W_0$-W, $W_0$-W-R or $W_0$-R-W with the arrangement listed as the arrangement of electrodes would appear from the open end of the laminated body to the vent opening. The preferred position was found to be R-W-$W_0$; that is, as the sample fluid entered the open end of the laminated body, the fluid would cover R first, then W, then $W_0$.

The second electrode, $W_0$, is positioned so that the sample fluid reaches it last. The resulting current at $W_0$ thus triggers the reading meter to start the measurement and analyte concentration determination process. Such an arrangement obviates reliability and accuracy problems due to an insufficient sample fluid size. It should be pointed out that $W_0$ can also be used as a counter electrode. The resulting three-electrode system (i.e. working electrode, reference electrode and counter electrode) would be used in the case of a sample fluid having high resistance. It should also be pointed out that $W_0$, combined with R, can be used to measure the resistance of the sample fluid. The resulting resistance could be used to estimate the hematocrit of a blood sample and therefore to correct the measurement for hematocrit effect.

Creatinine Sensor

Preparation of Reagents 1, 2 and 3

Reagents 1, 2 and 3 comprise the reduced form of a redox mediator, a binder, and a surfactant. The reduced form of the redox mediator must be stable in the reagent matrices and must make the reference electrode function well. Its quantity in the formulation must be sufficient to attain a working linear range. The preferred redox mediator is potassium ferrocyanide. The binder should be sufficiently water-soluble and should also be capable of stabilizing and binding all other chemicals in the reagents in electrode areas W1, W2 and R to the conductive surface/layer 21 of base layer 20. The binders are polyethylene oxide and various water soluble cellulose materials. The preferred binder is methyl cellulose and is available as Methocel 60 HG (Cat. No. 64655, Fluka Chemical, Milwaukee, Wis.). Preferably, a small amount of anti-oxidant is added to Reagents 1, 2 and 3. The anti-oxidant stabilizes the redox mediator, thus providing for a long-term shelf-life. The anti-oxidant must not interfere with the enzymatic reactions (Eqs. (1) to (4)) and the ensuing amperometric measurement. The preferred anti-oxidant is sodium sulfite and is available from most chemical supply companies. The surfactant is necessary to facilitate dispensing of Reagents 1, 2 and 3 into the cutouts for W1, W2 and R as well as for quickly dissolving the dry chemical reagents. The amount and type of surfactant is selected to assure the previously mentioned function and to avoid a denaturing effect on the enzymes. The preferred surfactant is a polyoxyethylene ether. More preferably, it is t-octylphenoxypolyethoxyethanol and is available under the brand name Triton X-100.

Reagent 2, in addition to the components in Reagent 1, contains creatine amidinohydrolase (C-IIAT, 14 U/mg, Kikkoman, Japan), sarcosine oxidase (SOD-TE, about 33 U/mg, Kikkoman, Japan) and soybean peroxidase (SBP-MD, about 220 U/mg, Organic Technologies, Columbus, Ohio.). Reagent 3, in addition to the components in Reagent 2, contains creatinine amidohydrolase (C-IE, about 600 U/mg, Kikkoman, Japan). The reagents are prepared as follows:

Reagent 1

Step 1: Prepare a 1% (W/W) Methocel 60 Hg solution by stirring 1 gram of Methocel 60 HG in 100 ml of water for 4 hours.
Step 2: Add 0.2 ml of 10% Triton X-100 into the methocel solution from Step 1.
Step 3: While stirring, add 2 grams of potassium ferrocyanide and 0.05 gram sodium sulfite to the solution from Step 2.

Reagent 2

Step 1-Step 3: Same as Reagent 1.
Step 4: While stirring, add 0.5 gram of soybean peroxidase to the solution from Step 3.
Step 5: Add 2 gram of creatine amidinohydrolase to the solution from Step 4.
Step 6: Add 0.5 gram of sarcosine oxidase to the solution from Step 5.

Reagent 3

Step 1-Step 6: Same as Reagent 2.
Step 7: While stirring, add 0.4 gram of creatinine amidohydrolase to the solution from Step 6.

Creatinine Electrode Construction

A piece of a gold or tin oxide/gold polyester film available from Courtaulds Performance Films is cut to shape, as illustrated in FIG. 2, forming base layer 20 of sensor 10. A conductive side of the gold or tin oxide/gold polyester film is scored. Scribing or scoring the conductive layer may be done mechanically, by laser or by any other method to create three independent conductive paths. Preferably, a YAG, eximer or $CO_2$ laser is used. More preferably, the conductive layer is scored by $CO_2$ laser (25W laser available from Synrad, Inc., San Diego, Calif.). As illustrated in FIG. 2, the film is scored by the laser such that three electrodes at sample fluid end 110 and three contact points 122, 124 and 126 are formed at electrical contact end 120. The scoring line is very thin but sufficient to create three separate electrical conductors. A scoring line 28 can be made, but is not necessary, along the outer edge of base layer 20 to avoid potential static problems which could cause a noisy signal from the finished sensor 10.

As mentioned earlier, the conductive conduits may be deposited on the insulating layer by screen printing, by vapor deposition, or by any method that provides a conductive layer which adheres to the base insulating layer. Other conductive coatings may also be used such as palladium film or other noble metal film or their oxides or a carbon film composition.

A piece of one-sided adhesive tape, having a thickness preferably of about 0.0025 in. (0.06 mm), is then cut to size and shape forming first middle layer 30 so that it will cover a majority of the conductive layer 21 of base layer 20 except for exposing a small electrical contact area illustrated in FIG. 1. Three rectangular, square or circular cutouts 32, 34 and 36 of substantially equal size are punched by $CO_2$ laser or die-cut. Cutouts 32, 34 and 36 define the electrode areas W1, W2 and R, which hold chemical reagents. The size of the cutouts is preferred to be made as small as possible in order to make the fluid sample channel 112 of sensor 10 as short as possible while still being capable of holding sufficient chemical reagent to function properly. The preferred hole is round in shape and has a diameter of about 0.043 in. (1.1 mm). As illustrated in FIG. 2, cutouts 32, 34 and 36 are aligned with each other and have a spacing of about 0.026 in. (0.65 mm) between them. The circular cutouts are for illustrative purposes only. It should be understood that the shape of the cutouts is not critical provided that the size of the cutouts is big enough to facilitate dispensing chemical reagents but small enough to allow for a reasonably small sample channel. As stated previously, the preferred arrangement of the electrodes formed in cutouts 32, 34 and 36 is W1 (working electrode 1), R (reference electrode) and W2 (working electrode 2). The surface of the first middle layer 30 must be sufficiently hydrophilic. This is achieved by coating a layer of hydrophilic polymer or surfactant onto the first middle layer. Preferably, the non-sticky side, which will face up to the fluid channel, is treated or coated with a surfactant (e.g. 0.05 % Triton X-100). A piece of the one-sided adhesive tape is cut to shape as depicted in FIG. 1 so that it will cover a majority of conductive base layer 20 except for exposing a small electric contact area (3×6 mm) and three cutouts defining electrode areas R, W1 and W2.

0.5 microliter of Reagent 1 is dispensed into electrode area R. Reagent 1 is a mixture of a redox mediator, a binder/stabilizer and a surfactant. The preferred mixture for Reagent 1 is made by mixing the following components in the described percentages (W/W %): about 2% potassium ferrocyanide, about 1% Methocel 60 HG, about 0.05% sodium sulfite, about 0.02% Triton X-100.

0.5 microliter of Reagent 2 is dispensed into electrode W1. Reagent 2 is a mixture similar to that of Reagent 1 but with the addition of three enzymes, i.e. C2, SO and SBP, capable of catalyzing a reaction involving a substrate of creatine. The preferred mixture for Reagent 2 is made by mixing the following percentages (W/W %) of the following ingredients: about 2% C2, about 0.5% SO, about 0.5% SBP, about 2% potassium ferrocyanide, about 1% Methocel 60 HG, about 0.05% sodium sulfite, about 0.02% Triton X-100.

0.5 microliter of Reagent 3 is dispensed into electrode W2. Reagent 3 is a mixture similar to that of Reagent 2 but with the addition of an enzyme, e.g. C1, capable of catalyzing a reaction involving a substrate of creatinine. The preferred mixture for Reagent 3 is made by mixing the following percentages (W/W %) of the following ingredients: about 0.4% C1, about 2% C2, about 0.5% SO, about 0.5% SBP, about 2% potassium ferrocyanide, about 1% Methocel 60 HG, about 0.05% sodium sulfite, about 0.02% Triton X-100.

After the addition of the reagents to the electrode areas, the device is dried in an oven for about 5 minutes at 37° C. After drying, a piece of double-sided tape, having a thickness preferably of about 0.007 in. (0.18 mm) and available from Adhesive Research, Inc. (Cat. No. X12314), is cut into shape with a U-shape notch cutout at one end as illustrated in FIG. 2. The preferred size of the cutout is about 0.264 in. (6.7 mm) long by about 0.065 in. (1.65 mm) wide. The double-sided tape serves as a spacer layer and is second middle layer 40. The U-shape cutout is made with the $CO_2$ laser described earlier. The thickness of the double-sided tape along with the length and width of the cutout defines the volume size of the fluid sample channel and the relative speed the fluid sample moves into the defined chamber. The preferred size of the U-shaped cutout 42 is about 0.264 in. long (6.7 mm), about 0.065 in. wide (1.65 mm) and about 0.007 in. thick (0.18 mm).

A piece of a transparency film having a thickness preferably of about 0.0043 in. (0.11 mm)(Cat. No. PP2200 or PP2500 available from 3M) is fashioned into top layer 50. A rectangular vent hole 52 is made using the $CO_2$ laser or die-cut previously mentioned. The preferred size of vent hole 42 is about 0.065 in. (1.65 mm) by about 0.059 in. (1.50 mm). The center of vent hole 52 is located approximately 0.234 in. (5.95 mm) from fluid end 110 of sensor 10. Top layer 50 is aligned and layered onto second middle layer 40 to complete the assembly, as illustrated in FIG. 1, of sensor 10. Although the preferred embodiment is described, it should be understood that the present invention may have a variety of embodiments without detracting from the spirit of the present invention.

When a fluid sample is applied to a single strip of the present invention, the fluid sample enters the channel through sampling end aperture 114 and flows over W1, R and W2 and stops at the threshold of vent opening 52. The length of the fluid channel 112, i.e. from sampling end aperture 114 to the threshold of vent opening 52, is about 0.208 in. (5.2 mm). The volume of the channel is calculated to be 1.54 microliters.

Figure 6A:
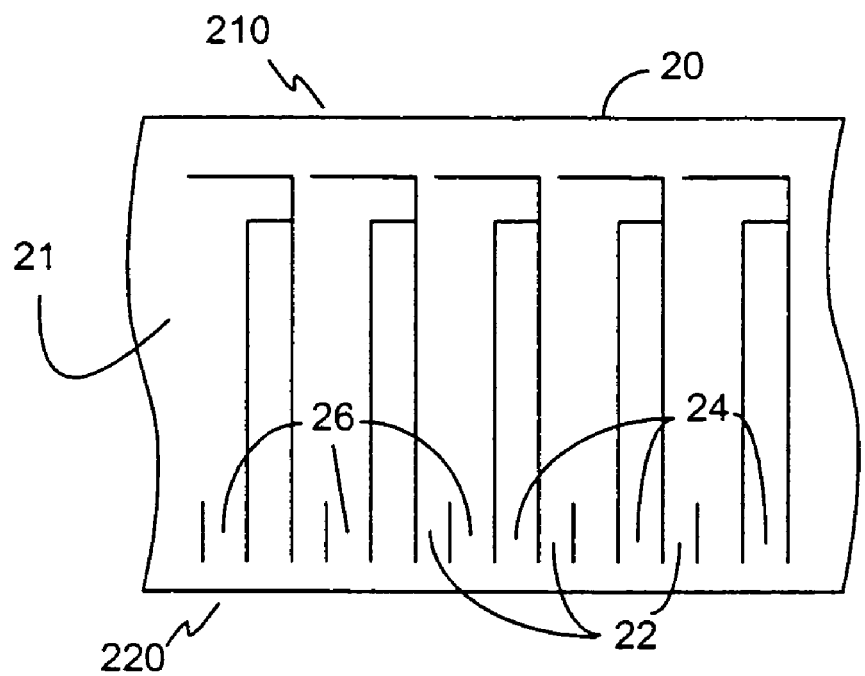
FIGS. 6A, 6B, 6C, and 6D are top views of a strip of each layer of the present invention showing the patterns for making multiple sensors of the four-layer embodiment.
Figure 6B:
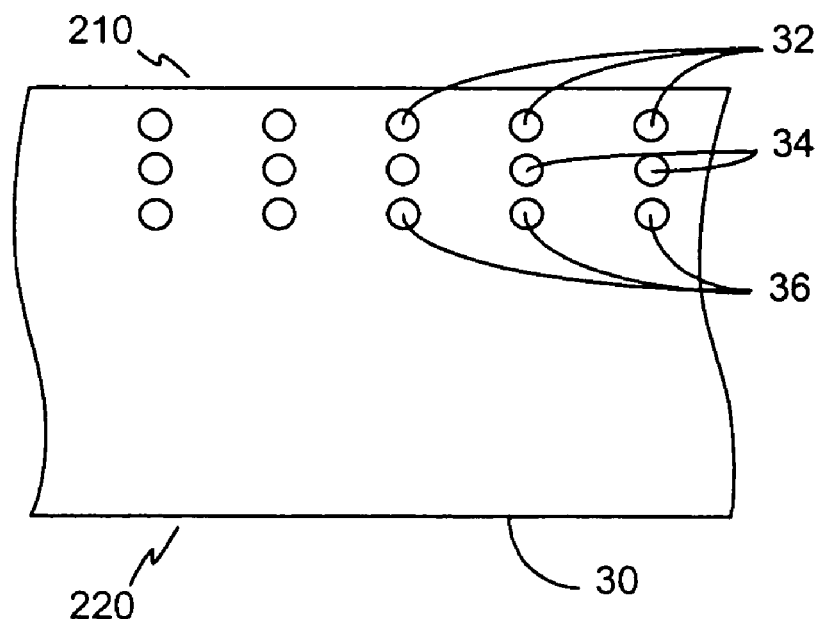

Although the description of electrode construction above describes construction for a single sensor, the design and materials used are ideal for making multiple sensors from one piece of each layer material as shown in FIGS. 6A-6E. This would be accomplished by starting with a relative large piece of base layer 20 having conducting layer 21 thereon. A plurality of scored lines are made into conductive layer 21 such that a repetitive pattern, as illustrated in FIG. 6A, is created using the preferred scribing method described previously whereby each pattern will eventually define the three conductive paths 22, 24 and 26 for each sensor. Similarly, a large piece of first middle layer 30, which is illustrated in FIG. 6B and which also has a plurality of cutouts 32, 34, and 36 in a repetitive pattern, is sized to fit over base layer 20 in such a way that a plurality of sensors 10 will be had when completed. The size of each cutout and the electrode material disposed in the plurality of electrode areas W1, R and W2 are similar to that disclosed above.

Figure 6C:
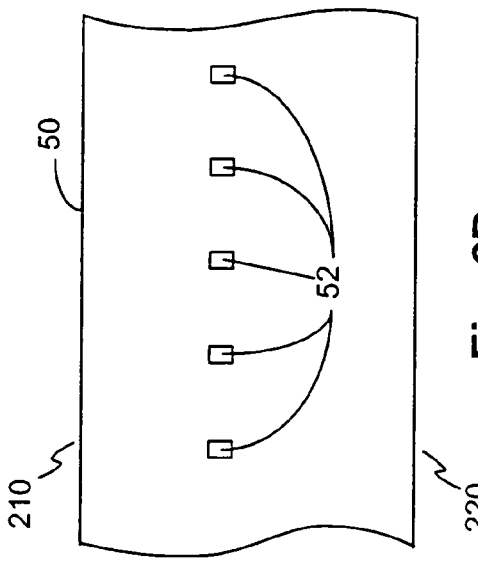
Figure 6D:
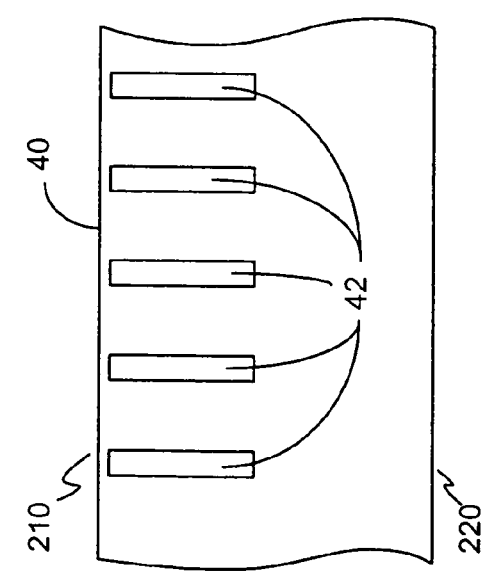
Figure 6E:
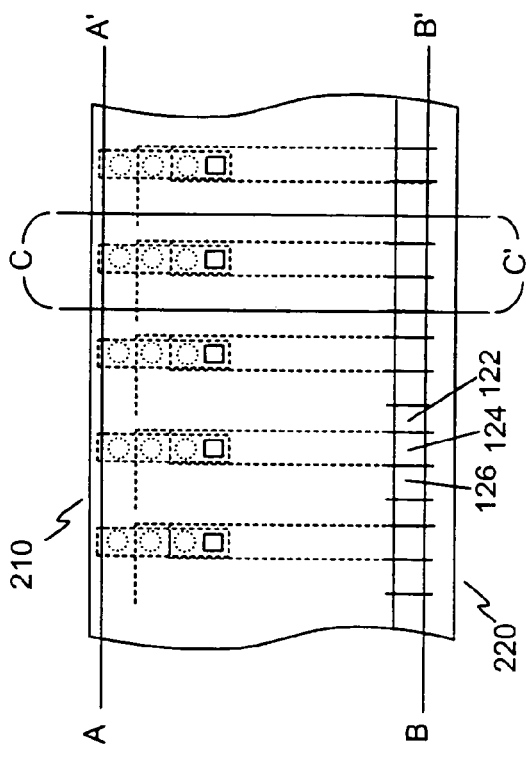
FIG. 6E is a top view of a segment of the laminated strip of the present invention showing the patterns for making multiple sensors of the four-layer embodiment.

After disposing Reagents 1, 2 & 3 in their respective cutouts and dried, a large piece of second middle layer 40 having a plurality of elongated cutouts 42 and illustrated in FIG. 6C is layered onto first middle layer 30 such that each elongated cutout 42 of second middle layer 40 contains corresponding cutouts 32, 34 and 36 of first middle layer 30. A comparably-sized top layer 50 having a plurality of vent openings 52 in a repetitive pattern, as shown in FIG. 6D, is layered onto second middle layer 40. FIG. 6E is a top view of the combined layers. The laminated strip created by the four layers 20, 30, 40 and 50 has a plurality of sensors 10 that can be cut from the laminated strip. The laminated strip is cut longitudinally along line A-A' at fluid sampling end 210 to form a plurality of sampling apertures 114 and longitudinally along line B-B' at electrical contact end 220 to form a plurality of conductive contacts 122, 124 and 126. The laminated strip is also cut at predetermined intervals along line C-C' forming a plurality of individual sensors 10.

Shaping of the fluid sampling end 120 of each sensor 10, as illustrated in FIG. 1, may be performed if desired. It should be understood by those skilled in the art that the order in which the laminated strip can be cut is not important. For instance, the laminated strip may be cut at the predetermined intervals (C-C') and then the cuts along A-A' and B-B' can be made to complete the process. Chronoamperometry (I-t curve) was used for measurement of the current response of the strips using an Electrochemical Analyzer (CH Instruments, Model 812, Austin, Tex.). If not stated otherwise, the current at 20 seconds was recorded.

The following examples illustrate the unique features of the present invention. A potential of −0.15 Volts was applied across the working electrodes and the reference electrode. The resultant current signals based on the oxidation of the reduced form of the redox mediator are representative of the creatine and creatinine concentrations in accordance with the preferred embodiment of the present invention.

EXAMPLE 1

Demonstration of Linear Range

Sample strips of the present invention were first tested in phosphate buffer solution (PBS) containing 0 to 15 mg/dL creatinine with an Electrochemical Analyzer (CH Instruments, Model 812, Austin, Tex.). Table 1A shows the measured current response in nanoamperes of a sensor of the present invention to varying concentrations of creatinine in phosphate buffer solution.

TABLE 1A

Response for Creatinine in PBS

| Concentration (mg/dL) | Current (nA) |
| --- | --- |
| 0.0 | 0.0 |
| 0.2 | 4 |
| 0.4 | 12.5 |
| 0.6 | 25 |
| 1 | 51 |
| 2 | 123 |
| 3 | 182 |
| 5 | 263 |
| 10 | 472 |
| 15 | 520 |

Figure 7A:
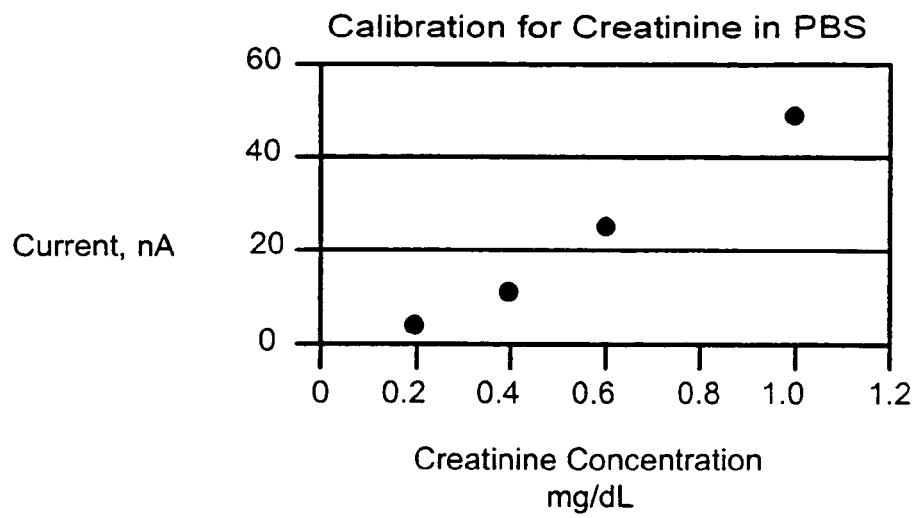
FIGS. 7A and 7B displays response curves for a creatinine sensor of the present invention in phosphate buffer solution.
Figure 7B:
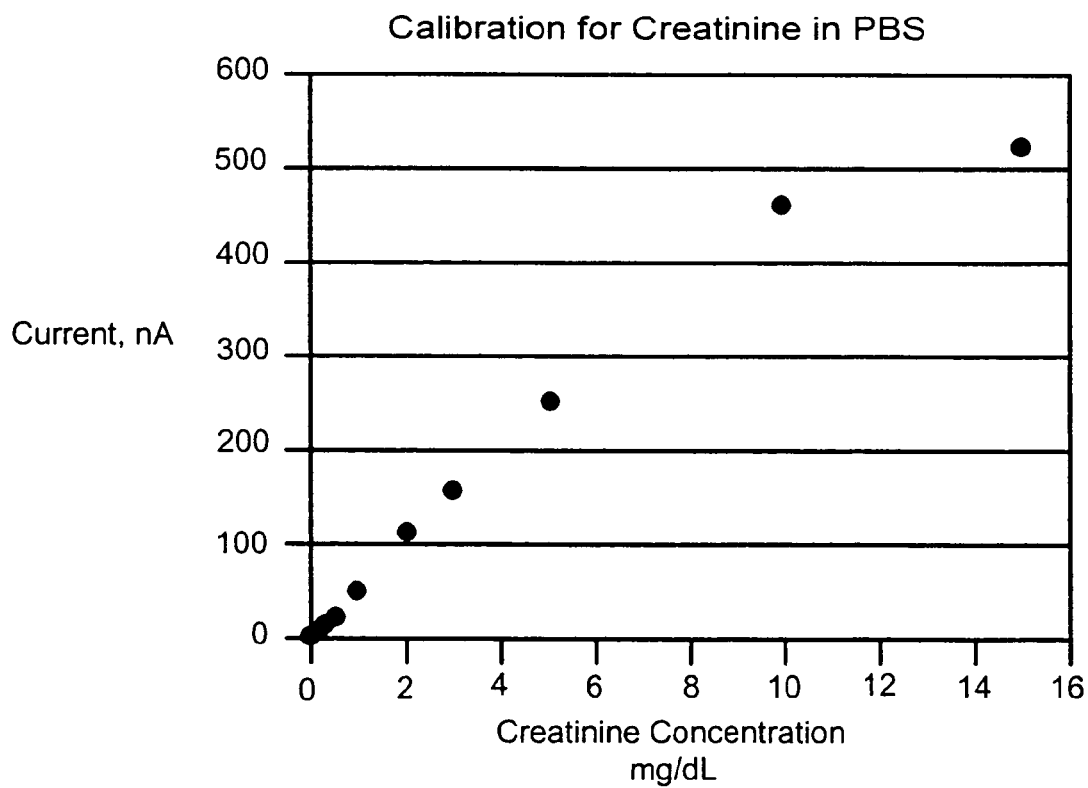

A graphical representation of the above data is shown in FIGS. 7A and 7B. FIG. 7A is an enlarged view of the graphical representation for creatinine concentrations of 0 to 1 mg/dL. As seen from the data and the graphs, the sensors of the present invention respond to small amounts of creatinine as low as 0.2 mg/dL. The sensors also exhibit a linear relationship of current response versus creatinine concentration over a concentration range from about 0.2 to about 10 mg/dL.

In order to test the response of the strips in a real sample, a sample of venous blood was collected and separated into several aliquots. Each aliquot was spiked with different creatinine concentrations ranging from 0 to 25 mg/dL. The aliquots were each measured using a sensor of the present invention with the Electrochemical Analyzer. Table 1B shows the current response in nanoamps in a blood sample spiked with varying levels of creatinine.

TABLE 1B

Response for Creatinine in Blood

| mg/dL (C) | nA (I) |
| --- | --- |
| 0 | 21 |
| 1 | 46 |
| 2 | 72 |
| 5 | 150 |
| 10 | 310 |
| 15 | 440 |
| 20 | 536 |
| 25 | 623 |

Figure 8:
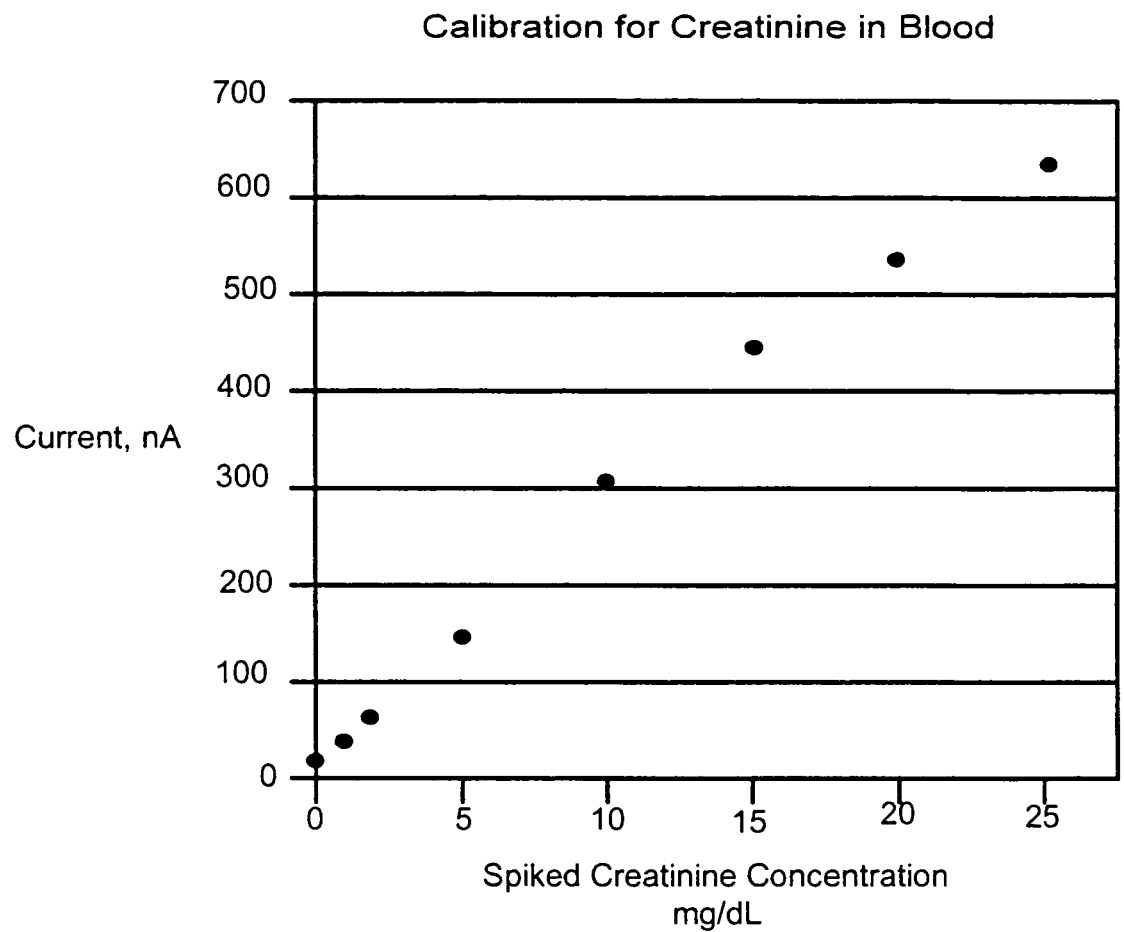
FIG. 8 is a response curve using creatinine sensors of the present invention for blood samples.

A graphical representation of the test data is shown in FIG. 8. The test results indicate that the sensors of the present invention have a linear response (current response vs. creatinine concentration) over a creatinine concentration range from about 0 to about 20 mg/dL, but continue to respond above this range.

EXAMPLE 2

Demonstration of Precision of Sensors

The precision of the sensors of the present invention was investigated at the creatinine level of 2 mg/dL in a blood sample. The creatinine level was confirmed by measurement using the Nova Stat Profile M, Nova Biomedical Co., Waltham, Mass. Table 2 shows the current response in nano-amps of a blood sample spiked with 2 mg/dL of creatinine using various sensors of the present invention.

TABLE 2

Precision Study

| Run No. | Current (nA) |
| --- | --- |
| 1 | 55 |
| 2 | 55 |
| 3 | 55 |
| 4 | 61 |
| 5 | 55 |
| 6 | 55 |
| 7 | 59 |
| 8 | 53 |
| 9 | 59 |
| 10 | 56 |
| 11 | 56 |
| 12 | 59 |
| 13 | 60 |
| 14 | 62 |
| 15 | 62 |
| 16 | 62 |
| 17 | 60 |
| 18 | 57 |
| 19 | 60 |
| 20 | 62 |
| 21 | 59 |

Average 58.2 CV, % 5.0

Twenty-one (21) sensor strips from the same batch were tested and a coefficient of variation (CV) was found to be 5.0%.

EXAMPLE 3

Demonstration of Interference Free Feature

The most important challenge for the measurement of creatinine is the interference from creatine, as it always co-exists in the sample along with creatinine. The unique design of the present invention makes it possible to eliminate the interference from creatine. This is achieved by subtracting the response obtained at W1 from the response obtained at W2, and is represented by the following equation:

$$I = Iw_2 - Iw_1 \quad \text{Eq.(7)}$$

where $Iw_2$ is the current at W2 (second working electrode)

$Iw_1$ is the current at W1 (first working electrode)

I is the difference between W2 and W1 and represents the current due to oxidation of the mediator of its reduced form, which is proportional to the creatinine concentration in the sample Because W1 and W2 have the same surface area, the potential interference present in the sample fluid should give relatively identical signals from each working electrode.

Figure 9:
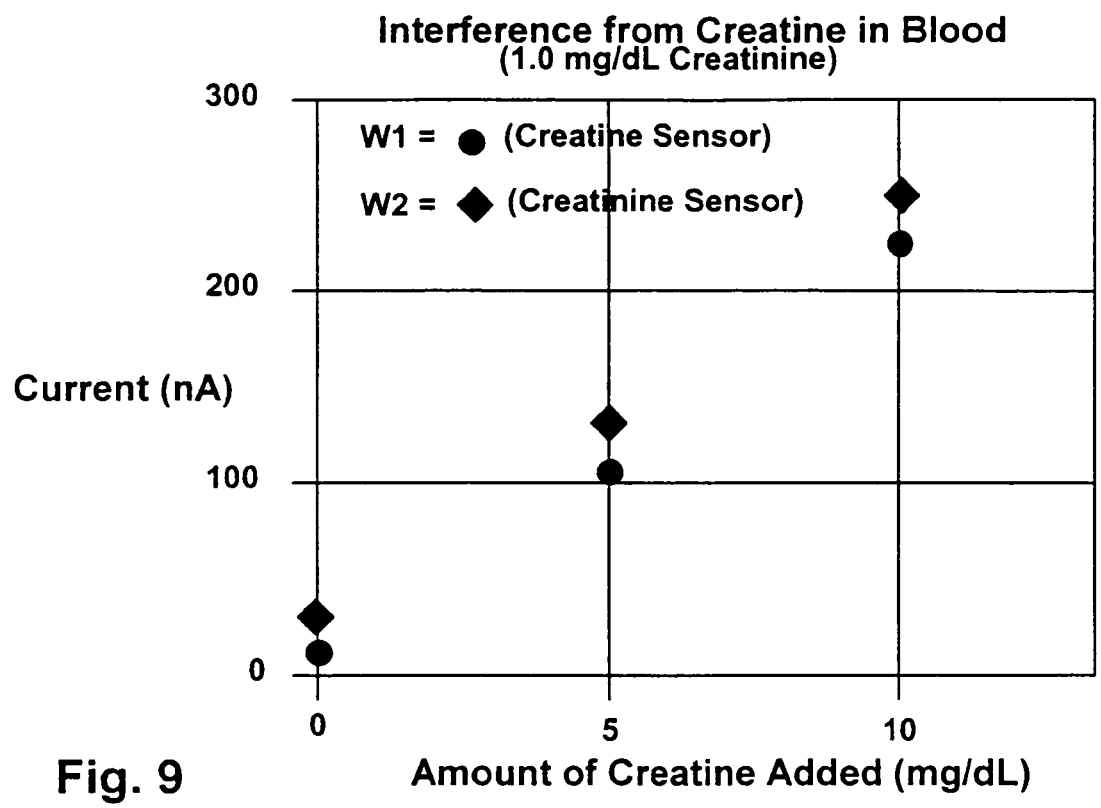
FIG. 9 is a response curve of a creatinine sensor of the present invention showing the response to creatine and creatinine.

This was tested by spiking a blood sample with different concentrations of creatine, i.e. (A) blood sample (1.0 mg/dL creatinine, measured with Nova Stat Profile M, Nova Biomedical Corporation, Waltham, Mass.); (B) same as (A) but with addition of 5 mg/dL creatine; (C) same as (A) but with the addition of 10 mg/dL creatine. FIG. 9 displays the effect of added creatine on the current response of the strips of the present invention. It is noticed that, although the sensor output currents increase upon spiking with creatine, the current difference at W2 and W1, representative of the analyte creatinine, remains nearly unchanged.

Other common interferences are from oxidizable substances such as ascorbic acid and acetaminophen present in the sample. A blood sample was spiked with different levels of ascorbic acid and acetaminophen. Table 3 shows the test results obtained.

TABLE 3

Response Change Upon Addition of Interferent

| mM | Current (nA) |
|---|---|
| 2 mg/dL creatinine; ascorbic acid | |
| 0.0 | 26 |
| 0.1 | 25 |
| 0.2 | 21 |
| 2 mg/dL creatinine; acetaminophen | |
| 0.0 | 32.5 |
| 1.0 | 34 |

The result shows that less than 0.1 mM ascorbic acid and 1 mM acetaminophen will not influence the measurement of creatinine due to the low level of applied potential (−0.15 V) previously described. These substances are not oxidized at that level of applied potential.

EXAMPLE 4

Demonstration of Minimum Sample Volume Feature

The unique design of the present invention enables the measurement of sample sizes smaller than have heretofore been possible. Blood samples are applied to the sensors and the samples travel along the sample fluid channel to the threshold of the vent hole. In order to test the volume effect on sensor response, different blood sample volumes were applied to the sensors. Table 4 shows the current response versus volume size.

TABLE 4

Response to Sample Volume

| Volume (uL) | Current (nA) |
|---|---|
| 1.5 | 60 |
| 2 | 59 |
| 3 | 58 |
| 4 | 55 |
| 5 | 55 |

Figure 10:
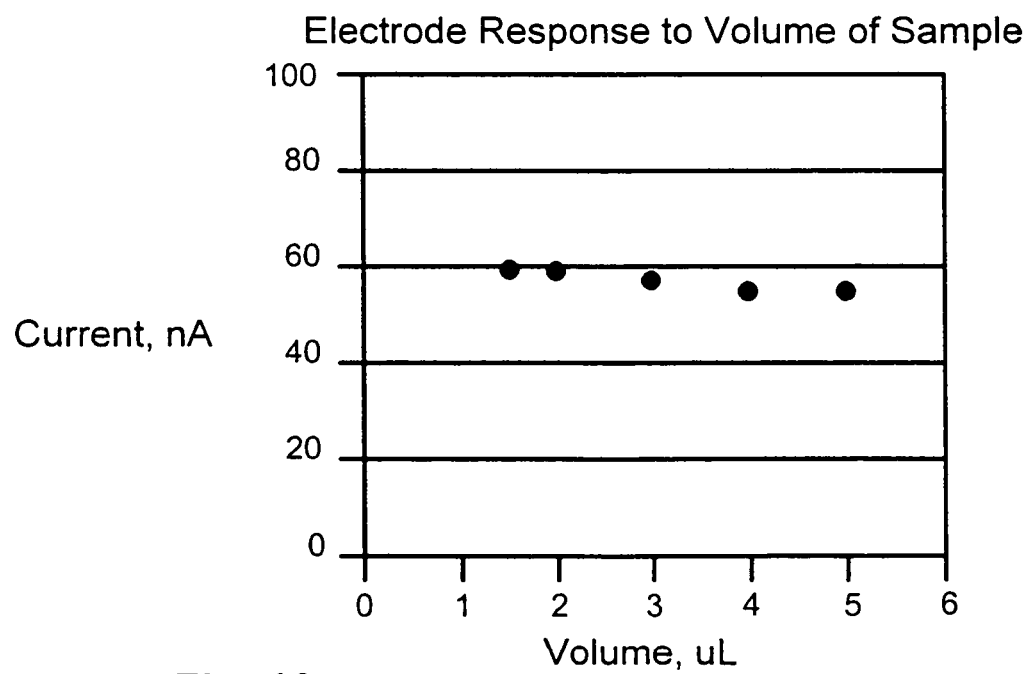
FIG. 10 is a graph of the response to volume sample of a creatinine sensor of the present invention.

The resulting current signals were plotted against volume and is shown in FIG. 10. From the data and the graphical representation, sensors of the present invention for the sizes disclosed earlier show no dependence of the response on the sample volume if the volume is above 1.5 microliters.

Glucose and Cholesterol Sensors

Preparation of Reagents

Reagents for both Glucose and Cholesterol Sensors comprise the reduced form of a redox mediator, a peroxidase, at least one binder, a surfactant, and at least one analyte-based enzyme. The preferred redox mediator is potassium ferrocyanide. The preferred peroxidase is soybean peroxidase and is available as SBP-MD (about 220 U/mg, Organic Technologies, Columbus, Ohio.). The preferred binder for the glucose sensor is methyl cellulose and is available as Methocel 60 HG (Cat. No. 64655, Fluka Chemical, Milwaukee, Wis.). The preferred binder for the cholesterol sensor is also a cellulose material and is available as Klucel®-EF (Hercules, Wilmington, Del.). Preferably, a small amount of anti-oxidant is added to the Reagents for the glucose and cholesterol sensors. The preferred anti-oxidant is sodium sulfite. The preferred surfactant is a polyoxyethylene ether. More preferable, it is t-octylphenoxypolyethoxyethanol and is available under the brand name Triton X-100.

For the glucose sensor, the analyte-based enzyme is glucose oxidase and is available as GO3AC from Biozyme, San Diego, Calif. For the cholesterol sensor, the analyte-based enzyme is a mix of cholesterol esterase available as COE-311 from Toyobo, Japan, and cholesterol oxidase available as COO-311, Toyobo, Japan.

The preferred reagent mixture for the glucose sensor is made by mixing the following components in the described percentages (W/W %): About 0.5% glucose oxidase, about 0.5% soybean peroxidase, about 2% potassium ferrocyanide, about 1% Methocel 60 HG, about 0.1% sodium sulfite, and about 0.02% Triton X-100.

The preferred reagent mixture for the cholesterol sensor is made by mixing the following components in the described percentages (W/W %): About 1% cholesterol esterase, about 2% cholesterol oxidase, about 0.5% soybean peroxidase, about 5% potassium ferrocyanide, about 1% Klucel-EF, about 0.1% sodium sulfite, and about 0.02% Triton X-100.

Glucose and Cholesterol Electrode Construction

The construction of the glucose and cholesterol sensors is based on the second embodiment previously described and illustrated in FIGS. 3 and 4. A piece of a gold or tin oxide/gold polyester film available from Courtaulds Performance Films is cut to shape, as illustrated in FIGS. 3 and 4, forming base layer 520 of sensor 500. A $CO_2$ laser is used to score the gold or tin oxide/gold polyester film (25 W laser available from Synrad, Inc., San Diego, Calif.). As illustrated in FIG. 4, the film is scored by the laser creating scoring line 527 and 528 such that three electrodes at sample fluid end 610 and three contact points 622, 623 and 624 were formed at electrical contact end 620. The scoring line is very thin but sufficient to create two separate electrical conductors. An additional scoring line 529 made be made, but is not necessary, along the outer edge of base layer 520 to avoid potential static problems which could cause a noisy signal from the finished sensor 500.

A piece of double-sided tape (Arcare® 7840) available from Adhesive Research, Glen Rock, Pa., is cut to size and shape forming middle layer 530 with U-shaped channel 532 so that it will cover a majority of the conductive layer 521 of base layer 520 except for exposing a small electrical contact area at electrical contact end 620 illustrated in FIG. 3. The U-shaped channel 532 is cut by using the $CO_2$ laser. Middle layer 530 is then layered onto base layer 520. As mentioned earlier, this middle layer 530 serves as a spacer and defines the size of the fluid sample channel 612. It also defines the electrode area 526 that holds the electrode reagent matrix 550. Its width and length is optimized to provide for a relatively quick moving fluid sample. The preferred size of U-shaped channel 532 is about 0.039 in. (1.0 mm) wide by about 0.134 in. (3.4 mm) long.

1.0 microliter of reagent mix is dispensed into channel 532 to form electrodes W, R and $W_0$. The reagent mix is a mixture of a redox mediator, a peroxidase, a binder, a surfactant, and at least one analyte-based enzyme. The preferred composition for the reagent mix is made by mixing the ingredients disclosed above for the glucose and cholesterol sensors. After the addition of the reagent mix, the devices were dried in an oven at 37° C. for about 5 minutes.

After drying, a piece of a transparency film (Cat. No. PP2200 or PP2500 available from 3M) is fashioned into top layer 540. A rectangular vent hole 542 is made using the $CO_2$ laser previously mentioned. The preferred size of vent hole 542 is about 0.039 in. (1.0 mm) by about 0.051 in. (1.30 mm). Vent hole 542 is located approximately 0.087 in. (2.2 mm) from fluid end 610 of sensor 500. Top layer 540 is aligned and layered onto middle layer 530 to complete the assembly, as illustrated in FIG. 3, of sensor 500.

EXAMPLE 5

Demonstration of Response to Glucose

Sample strips of the present invention were first tested in phosphate buffer solution (PBS) containing 0 to 20 mg/dL glucose with an Electrochemical Analyzer (CH Instruments, Model 812, Austin, Tex.). Table 5A shows the measured current response in nanoamperes of a sensor of the present invention to varying concentrations of glucose in phosphate buffer solution.

TABLE 5A

| Response for Glucose in PBS | |
| --- | --- |
| Concentration (mg/dL) | Current (nA) |
| 0.0 | 3 |
| 0.5 | 6 |
| 1 | 10 |
| 2 | 20 |
| 5 | 41 |
| 10 | 83 |
| 20 | 128 |

Figure 11:
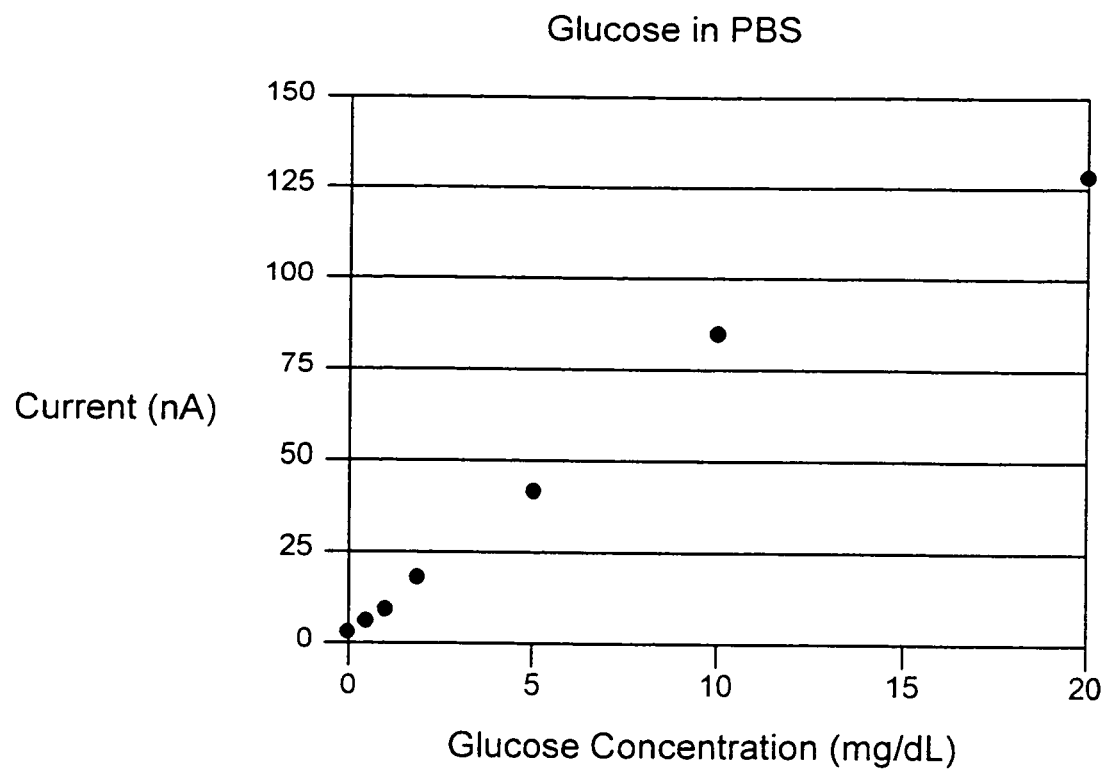
FIG. 11 is a response curve of a glucose sensor of the present invention in phosphate buffer.

A graphical representation of the above data is shown in FIG. 11. As seen from the data and the graph, the sensors of the present invention respond to small amounts of glucose and exhibit a near-linear relationship of current response versus glucose concentration over a concentration range from about 0.0 to about 20 mg/dL.

In order to test the response of the strips in a real sample, urine was collected and separated into several aliquots. Each aliquot was spiked with different glucose concentrations ranging from 0 to 50 mg/dL. The aliquots were each measured using a sensor of the present invention with the Electrochemical Analyzer. Table 5B shows the current response in nanoamps in a urine sample spiked with varying levels of glucose.

TABLE 5B

| Response for Glucose in Urine | |
| --- | --- |
| mg/dL (C) | nA (I) |
| unspiked | 10 |
| 10 | 24 |
| 20 | 35 |
| 50 | 74 |
| 100 | 96 |

Figure 12:
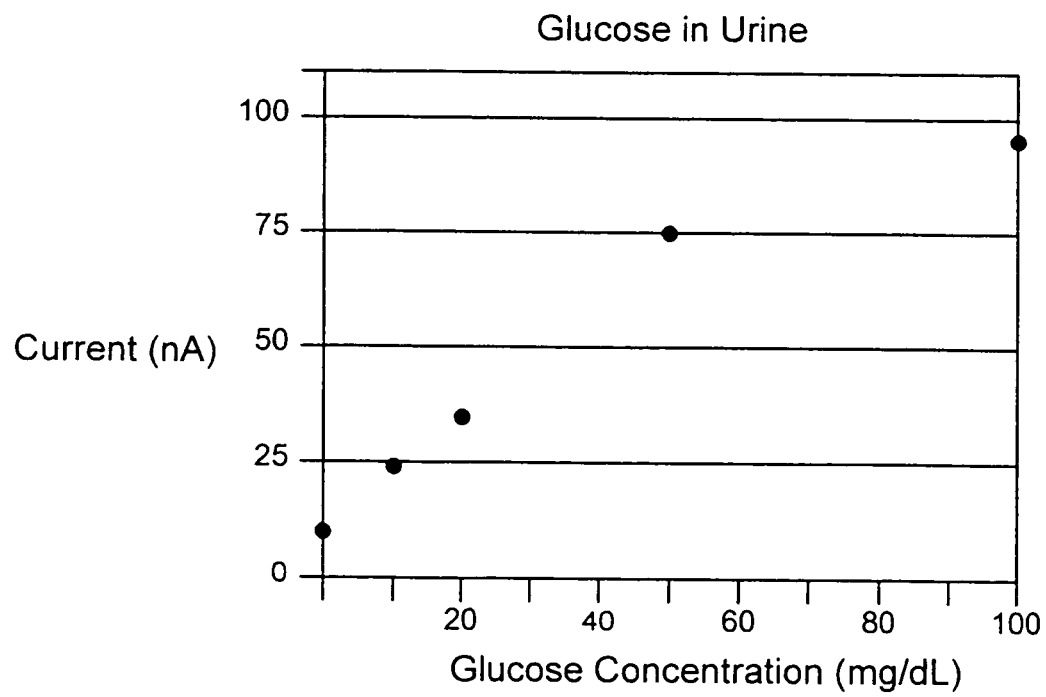
FIG. 12 is a response curve of a glucose sensor of the present invention in urine.

A graphical representation of the test data is shown in FIG. 12. The test results indicate that the sensors of the present invention have a linear response (current response vs. glucose concentration) over a glucose concentration range from about 0 to about 50 mg/dL, but continue to respond above this range.

EXAMPLE 6

Demonstration of Response to Cholesterol

Sample strips of the present invention were first tested in a Sigma calibration standard diluted with phosphate buffer solution (PBS) containing 0 to 200 mg/dL glucose with an Electrochemical Analyzer (CH Instruments, Model 812, Austin, Tex.). Table 6 shows the measured current response in nanoamperes of a sensor of the present invention to varying concentrations of cholesterol in phosphate buffer solution.

TABLE 6

| Response for Cholesterol in PBS | |
| --- | --- |
| Concentration (mg/dL) | Current (nA) |
| 0 | 5 |
| 25 | 150 |
| 50 | 225 |

TABLE 6-continued

Response for Cholesterol in PBS

| Concentration (mg/dL) | Current (nA) |
|---|---|
| 100 | 300 |
| 200 | 330 |

Figure 13:
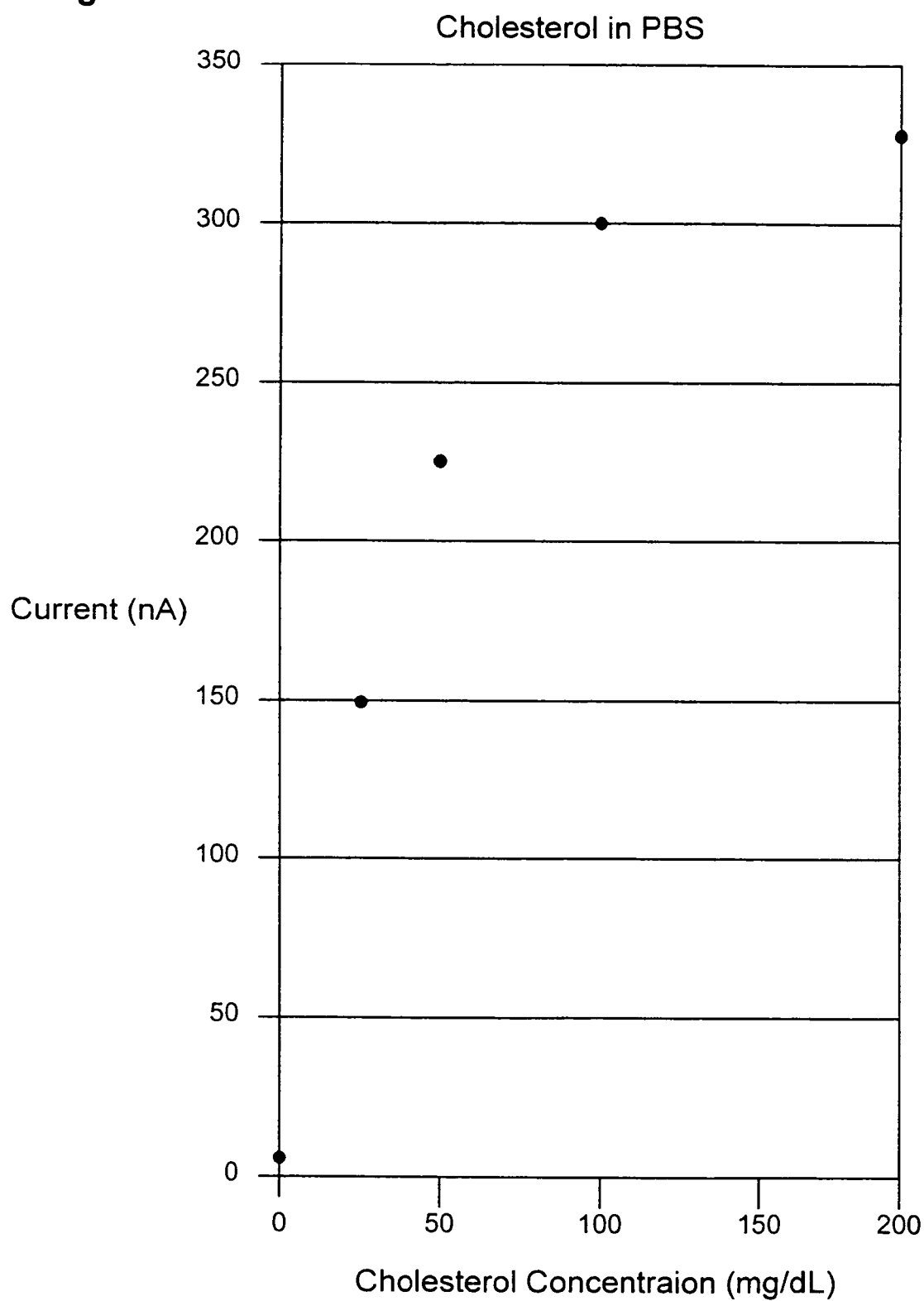
FIG. 13 is a response curve of a cholesterol sensor of the present invention in phosphate buffer.

A graphical representation of the above data is shown in FIG. 13. As seen from the data and the graph, the sensors of the present invention respond to small amounts of cholesterol and exhibit a near-linear relationship of current response versus cholesterol concentration over a concentration range from about 0.0 to about 200 mg/dL.

What is claimed is:

1. A method of using an electrode strip for determining the concentration of creatinine, said method comprising:
    obtaining an electrode strip comprising a first working electrode with a reagent matrix capable of measuring creatine in a liquid sample, a second working electrode with a reagent matrix capable of measuring creatine and creatinine in said liquid sample and a reference electrode wherein said reagent matrix of said first working electrode and said second working electrode are water-soluble and contain a peroxidase enzyme;
    disposing a fluid sample over said first working electrode, said second working electrode and said reference electrode of said electrode strip;
    applying a potential of 0.0V or less between said reference electrode and said first working electrode;
    measuring a first current generated between said first working electrode and said reference electrode and correlating said first current to a concentration of said creatine in said fluid sample;
    applying a potential between said reference electrode and said second working electrode;
    measuring a second current generated between said second working electrode and said reference electrode;
    subtracting said first current from said second current and obtaining a current difference whereby said current difference is representative of the concentration of creatinine in said fluid sample.

2. The method of claim 1 wherein said method further includes triggering said current measuring step when said fluid sample contacts said first working electrode, said second working electrode and said reference electrode creating said first current and said second current.

3. The method of claim 2 wherein said method further includes reading a current value for each of said first current and said second current at about a time where said current values for each of said first current and said second current reach a steady-state.

4. The method of claim 3 wherein said reading is taken at about 20 seconds after said current measuring step is triggered.

5. The method of claim 1 further comprising:
    measuring a resistance value of said liquid sample between said reference electrode and one of said first working electrode and said second working electrode;
    applying said resistance value to a first equation and determining the hematocrit level of said liquid sample; and
    calculating a corrected concentration of said analyte using a hematocrit equation to correct for the presence of hematocrit in said liquid sample.

6. A method of making a creatinine sensor comprising:
    obtaining a base strip of an insulating material, said base strip having a first end and a second end;
    disposing three conductive conduits between said first end and said second end;
    disposing a first middle layer of insulating material over said base strip, said first middle layer having three cutouts wherein each cutout exposes an electrode portion of each of said three conductive conduits wherein said three cutouts are spaced from said first end of said base strip, and wherein said first middle layer is sized to expose a contact portion of each of said three conductive conduits for a distance from said second end of said base strip;
    disposing a first reagent material on one of said three cutouts forming a first working electrode, a second reagent material on a second of said three cutouts forming a second working electrode and a reference material on a third of said three cutouts forming a reference electrode, wherein said first reagent material is made from mixing in water first and second enzymes wherein one of said first and second enzymes is a substrate of creatine, a redox mediator capable of reacting with a product of an enzymatic reaction involving said first and second enzymes, a peroxidase capable of catalyzing a reaction involving said redox mediator and said product wherein said redox mediator is oxidized, and said second reagent material is made from mixing in water said first and second enzyme, a third enzyme that is a substrate of creatinine, said redox mediator capable of reacting with a product of an enzymatic reaction involving said first and second enzymes and said third enzyme, said peroxidase capable of catalyzing a reaction involving said redox mediator and said product wherein said redox mediator is oxidized;
    solidifying said first reagent material and said second reagent material by removing a predefined quantity of said water from said first reagent material and said second reagent material;
    overlaying a second middle layer of insulating material over and coextensive with said first middle layer, said second middle layer having an elongated cutout portion where said elongated cutout portion exposes said three cutouts of said first middle layer; and
    disposing a top layer of insulating material over and coextensive with said second middle layer, said top layer having a vent opening wherein said vent opening exposes a portion of said elongated cutout portion furthest from said first end of said base strip.

7. The method of claim 6 further comprising drying said first reagent material and said second reagent material at a predetermined temperature and for a predetermined length of time sufficient to allow said first reagent material, said second reagent material and said reference reagent material to solidify and adhere to each of said electrode portions of said three conductive paths.

8. A method of making multiple, disposable creatinine sensors comprising:
    obtaining a base strip of an insulating material having a layer of conductive material disposed thereon, said base strip having a first edge and a second edge;
    scribing in said conductive material a plurality of lines in a repetitive pattern wherein said plurality of lines contain a repetitive pattern forming three conductive paths in each of said repetitive pattern;
    disposing a first middle layer of insulating material over said base strip, said first middle layer having a repetitive pattern of three cutouts wherein each cutout of each of said repetitive pattern exposes an electrode portion of each of said three conductive paths of each repetitive pattern wherein said repetitive pattern of said three cutouts are spaced from said first edge of said base strip, and wherein said first middle layer is sized to expose a contact portion of each of said three conductive paths of each repetitive pattern for a distance from said second edge of said base strip;

disposing a first reagent material on one of said three cutouts of each repetitive pattern forming a first working electrode, a second reagent material on a second of said three cutouts of each repetitive pattern forming a second working electrode and a reference material on a third of said three cutouts of each repetitive pattern forming a reference electrode, wherein said reference reagent material is made from a mixture of components in water comprising a redox mediator, said first reagent material is made from a mixture of components in water, said components being first and second enzymes, a redox mediator capable of reacting with a product of an enzymatic reaction involving said first and second enzymes, a peroxidase capable of catalyzing a reaction involving said redox mediator and said product wherein said redox mediator is oxidized, and said second reagent material is made from a mixture of components in water, said components being said first and second enzymes, a third enzyme that is a substrate of creatinine, said redox mediator capable of reacting with a product of an enzymatic reaction involving said first and second enzymes and said third enzyme, said peroxidase capable of catalyzing a reaction involving said redox mediator and said product wherein said redox mediator is oxidized;

drying said first reagent material, said second reagent material and said reference reagent material;

overlaying a second middle layer of insulating material over and coextensive with said first middle layer, said second middle layer having a plurality of elongated cutout portions in a repetitive pattern wherein each of said elongated cutout portions exposes a corresponding repetitive pattern of said three cutouts of said first middle layer;

disposing a top layer of insulating material over and coextensive with said second middle layer, said top layer having a plurality of vent openings in a repetitive pattern wherein each of said vent openings exposes a portion of a corresponding repetitive pattern of said elongated cutout portion furthest from said first edge of said base strip; and separating each of said repetitive pattern forming one of each of said disposable sensors.

9. The method of claim 8 further comprising drying said first reagent material, said second reagent material and said reference reagent material at a predetermined temperature and for a predetermined length of time sufficient to allow said first reagent material, said second reagent material and said reference reagent material to solidify and adhere to each of said electrode portion of each of said repetitive pattern of said three conductive paths.

10. The method of claim 9 further comprising cutting along said first edge of each of said sensors and transverse to said sensors a predetermined distance creating a sample inlet port.

* * * * *